(12) United States Patent
Tsuji et al.

(10) Patent No.: US 8,038,605 B2
(45) Date of Patent: Oct. 18, 2011

(54) BENDING CONTROL DEVICE

(75) Inventors: Kiyoshi Tsuji, Kunitachi (JP); Akira Taniguchi, Fuchu (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 1239 days.

(21) Appl. No.: 11/728,875

(22) Filed: Mar. 27, 2007

(65) Prior Publication Data

US 2007/0173694 A1  Jul. 26, 2007

Related U.S. Application Data

(63) Continuation of application No. PCT/JP2005/017593, filed on Sep. 26, 2005.

(30) Foreign Application Priority Data

Sep. 27, 2004 (JP) .................................. 2004-280080
Mar. 28, 2005 (JP) .................................. 2005-092600

(51) Int. Cl.
*A61B 1/00* (2006.01)
*A61B 1/04* (2006.01)

(52) U.S. Cl. ........................................ 600/152; 600/117

(58) Field of Classification Search .................. 600/141, 600/145, 146, 152
See application file for complete search history.

(56) References Cited

U.S. PATENT DOCUMENTS

| | | | |
|---|---|---|---|
| 4,899,731 A * | 2/1990 | Takayama et al. ............. | 600/145 |
| 4,982,725 A * | 1/1991 | Hibino et al. ................. | 600/117 |
| 5,334,207 A | 8/1994 | Gay, Jr. | |
| 5,373,317 A | 12/1994 | Salvati et al. | |
| 5,400,769 A * | 3/1995 | Tanii et al. .................... | 600/152 |
| 5,482,029 A * | 1/1996 | Sekiguchi et al. ............ | 600/109 |
| 5,492,131 A | 2/1996 | Galel | |
| 5,749,362 A * | 5/1998 | Funda et al. .................. | 600/407 |
| 5,957,833 A * | 9/1999 | Shan ............................. | 600/117 |
| 6,902,528 B1 * | 6/2005 | Garibaldi et al. ............ | 600/118 |
| 2002/0087048 A1 | 7/2002 | Brock et al. | |
| 2002/0183592 A1 * | 12/2002 | Suzuki et al. ................ | 600/145 |
| 2004/0034279 A1 | 2/2004 | Arai et al. | |
| 2004/0054258 A1 | 3/2004 | Maeda et al. | |

(Continued)

FOREIGN PATENT DOCUMENTS

JP  2000-079087  3/2000

(Continued)

OTHER PUBLICATIONS

European Office Action dated Feb. 23, 2010.

*Primary Examiner* — Philip Smith
(74) *Attorney, Agent, or Firm* — Scully, Scott, Murphy & Presser, P.C.

(57) ABSTRACT

At a distal end side of an insertion portion of an endoscope, an image pickup portion for capturing an image and a bending portion capable of being bent are provided, and a bending instruction operation portion executes a bending instruction operation for the bending portion. According to the bending instruction operation by the bending instruction operation portion, the bending control portion executes the controlling bending of the bending portion. As a bending control mode for executing the operation of the bending control by the bending control portion, a first bending control mode for bending control corresponding to a first image captured by the image pickup portion and a second bending control mode for bending control displaying the distal end side of the insertion portion are provided.

21 Claims, 15 Drawing Sheets

U.S. PATENT DOCUMENTS

| | | | |
|---|---|---|---|
| 2004/0116775 A1* | 6/2004 | Taniguchi et al. | 600/117 |
| 2004/0127769 A1* | 7/2004 | Hale et al. | 600/173 |

FOREIGN PATENT DOCUMENTS

| | | |
|---|---|---|
| JP | 2000-079088 | 3/2000 |
| JP | 2000-083889 | 3/2000 |
| JP | 2001-046332 | 2/2001 |
| JP | 2003-245246 | 9/2003 |
| JP | 2003-275168 | 9/2003 |
| WO | WO 97/44089 | 11/1997 |
| WO | WO 00/60996 | 10/2000 |
| WO | WO 03/028547 A2 | 4/2003 |
| WO | WO 03/086190 A1 | 10/2003 |
| WO | WO 2004/029782 A2 | 4/2004 |

* cited by examiner

BENDING CONTROL DEVICE

CROSS REFERENCE TO RELATED APPLICATION

This application is a continuation application of PCT/JP2005/017593 filed on Sep. 26, 2005 and claims the benefit of Japanese Applications No. 2004-280080 filed in Japan on Sep. 27, 2004 and No. 2005-092600 filed in Japan on Mar. 28, 2005, the entire contents of each of which are incorporated herein by their reference.

BACKGROUND OF THE INVENTION

1. Field of the Invention

The present invention relates to a bending control device for controlling bending of a bending portion provided at an insertion portion of an endoscope inserted into a body cavity.

2. Description of the Related Art

Recently, an endoscope has been widely employed in the medical field and others. At an insertion portion of the endoscope, a bending portion is provided in the vicinity of the base end of the distal end of the insertion portion so as to facilitate smooth insertion even into a bent body cavity. And when a direction to bend the bending portion is to be operated, an operator performs bending-operation of a bending operation knob provided at an operation portion or the like or a joystick or the like in case of an electrically bending endoscope disclosed in Japanese Unexamined Patent Application Publication No. 2003-245246.

In a conventional example, when the bending portion is to be bent, it is carried out according to an observation result of an endoscopic image captured by an image pickup device or the like provided at the distal end portion of the insertion portion. That is, the direction to bend the bending portion is determined depending on the direction where an image portion showing a lumen portion such as a digestive duct exists in the endoscopic image.

The image pickup device is mounted at the distal end portion in a predetermined direction, and when the endoscopic image captured by the image pickup device is to be displayed on display means such as a monitor, the up direction of the endoscopic image matches the up direction in the vertical and horizontal directions of the bending portion.

Therefore, the direction to bend the bending portion is determined by checking in which direction in the up, down, right and left directions an image portion where a lumen portion is displayed dark is located in the endoscopic image.

On the other hand, in order to insert the insertion portion of the endoscope more smoothly, an insertion shape of the insertion portion inserted into the body cavity may be displayed.

Japanese Unexamined Patent Application Publication No. 2000-79087, for example, discloses an endoscope system showing an endoscopic image and the insertion shape.

Japanese Unexamined Patent Application Publication No. 2000-79087 discloses the endoscopic image and the image of the insertion shape, but in this conventional example, the bending operation is made on the basis of an endoscopic image when bending the bending portion, and the image of the insertion shape is used only as its supplementary image.

In the meantime, when the direction of a lumen is not known in the endoscopic image, it would be very convenient if bending operation and controlling bending of the bending portion according to the bending operation can be made on the basis of the image of the insertion portion or other displayed images, which facilitates insertion work and the like.

SUMMARY OF THE INVENTION

A bending control device of the present invention comprises a bending instruction operation portion for executing bending instruction operation to a bending portion in an endoscope having an insertion portion provided with an image pickup portion for capturing an image and the bending portion capable of being bent at the distal end side; and a bending control portion for controlling bending of the bending portion according to the bending instruction operation by the bending instruction operation portion, wherein a first bending control mode for bending control corresponding to a first image captured by the image pickup portion; and a second bending control mode for bending control corresponding to a second image displaying the distal end side of the insertion portion are provided as the bending control mode for operation of the bending control by the bending control portion.

DETAILED DESCRIPTION OF THE PREFERRED EMBODIMENTS

Embodiments of the present invention will be described below referring to the attached drawings.

First Embodiment

A first embodiment of the present invention will be described referring to FIGS. 1 to 14.

Figure 1:
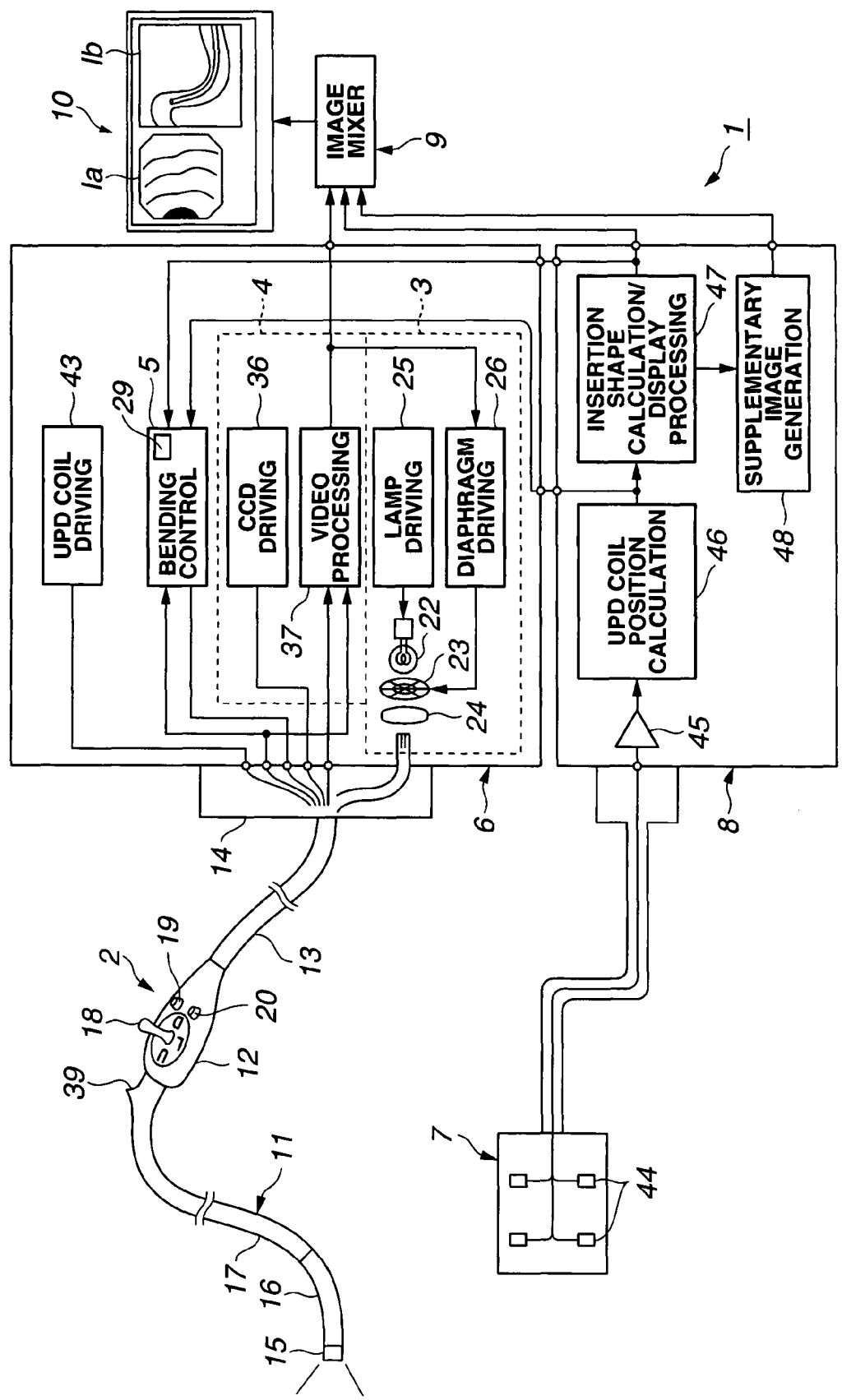
FIG. 1 is an entire configuration of an endoscope device provided with a first embodiment of the present invention.

As shown in FIG. 1, an endoscope device 1 provided with the first embodiment of the present invention comprises an endoscope 2 to be inserted into a body cavity or the like, a light source portion 3 for supplying illumination light to this endoscope 2, a signal processing portion 4 for signal processing to signal from image pickup means incorporated in the endoscope 2, and a video processor 6 incorporating a bending control device 5 and the like for controlling bending of a bending portion of the endoscope 2.

This endoscope device 1 further comprises an UPD coil unit 7 for detecting a position of insertion-shape detection coils (hereinafter abbreviated as UPD coils) provided at the endoscope 2, an insertion-shape detecting device (UPD device) 8 for generating an image of the insertion shape of the endoscope 2 from a detection signal from this UPD coil unit 7, an image mixer 9 for mixing an endoscopic image captured by the image pickup means and an insertion-shape detected image (UPD image) by the UPD device 8, and a high-definition monitor 10 such as a high-vision monitor for displaying two images mixed by this image mixer 9 in an aspect ratio of 16:9.

The endoscope 2 has an elongated insertion portion 11 to be inserted into the body cavity, an operation portion 12 provided at the rear end of this insertion portion 11, and a universal cord 13 extending from this operation portion 12, and a connector 14 at the rear end of this universal cord 13 is detachably connected to a video processor 6.

Also, the insertion portion 11 has a rigid distal end portion 15 provided at the distal end, a bending portion 16 provided adjacent to the rear end of this distal end portion 15 and capable of being bent, and a flexible tube portion 17 having flexibility extending from the rear end of this bending portion 16 to the front end of the operation portion 12.

At the operation portion 12, a joystick 18 for executing instruction operation of a bending direction and a bending angle of the bending portion 16, a bending-mode selection switch 19 for selecting (switching) a bending mode, and a scope switch 20 for executing instruction operation of still image display and the like.

Inside the insertion portion 11 or the like of this endoscope 2, a light guide 21 for transmitting illumination light is inserted, and the rear end of this light guide 21 protrudes from the connector 14 to become an incident end face of the illumination light.

To this incident end face, the illumination light by a lamp 22 incorporated in the light source portion 3 enters via a diaphragm 23 and a light-collecting lens 24. The lamp 22 is lighted by a lamp driving power supplied from a lamp driving circuit 25 and generates the illumination light.

Also, the diaphragm 23 has its opening amount (diaphragm amount) passing the illumination light controlled by a diaphragm control circuit 26.

The illumination light transmitted by the light guide 21 is outputted to the outside through a light-guide distal end face fixed to the distal end portion 15 of the insertion portion 11 and further through an illumination lens 27 mounted at an illumination window (See FIG. 7) for illuminating an affected portion or the like inside the body cavity.

Figure 2:
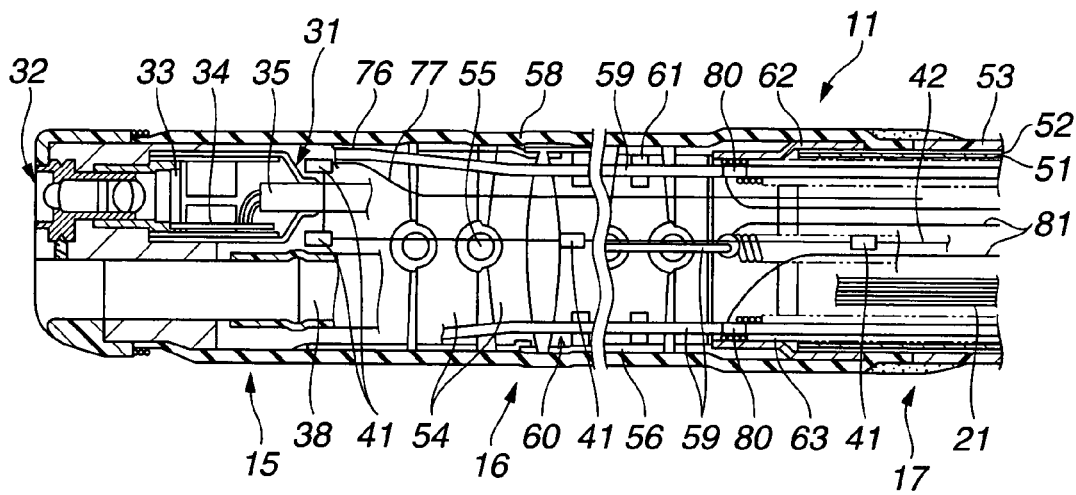
FIG. 2 is a longitudinal sectional view showing a construction of a distal end side of an insertion portion of an endoscope.

As shown in FIG. 2, an observation window is provided (adjacent to the illumination window) at the distal end portion 15, and an image pickup unit 31 is mounted at this observation window.

This image pickup unit 31 has an objective lens 32 mounted at a lens frame, a charge coupled device (abbreviated as CCD) 33 as an image pickup device with its image pickup face arranged at an image forming position by this objective lens 32, and a circuit board 34 arranged on the back face side of this CCD 33 and on which an electronic device forming an amplifier and the like is implemented.

And a cable 35 with its distal end side connected to the circuit board 34 and the like is inserted through the insertion portion 11 and the like and its rear end side is connected to a CCD driving circuit 36 and a video processing circuit 37 constituting the signal processing portion 4 through an electric contact of the connector 14 as shown in FIG. 1.

The CCD driving circuit 36 generates a CCD driving signal and applies this CCD driving signal to the CCD 33. The CCD 33 photoelectrically converts an optical image formed on the image pickup face upon application of the CCD driving signal and outputs it as a CCD output signal.

Figure 5:
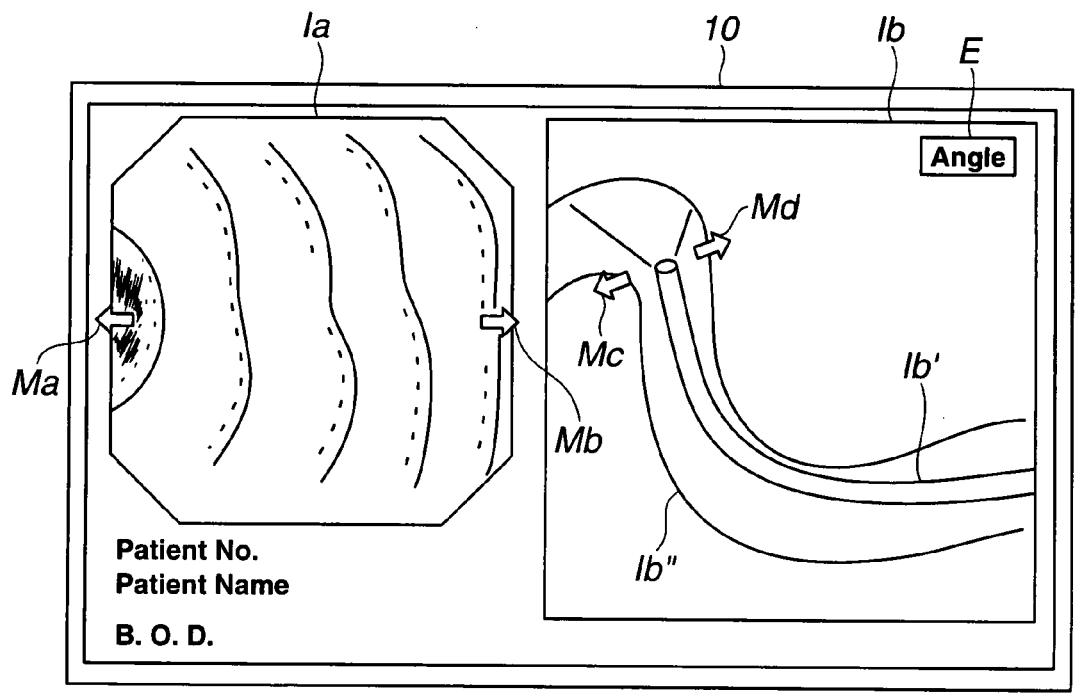
FIG. 5 is a diagram showing two images displayed on a high-definition monitor.

This CCD output signal is inputted to the video processing circuit 37, and the video processing circuit 37 generates a video signal of an endoscopic image captured by the CCD 33. And this video signal is outputted to the high-definition monitor 10 through the image mixer 9, and an endoscopic image Ia is displayed on a display screen of the high-definition monitor 10 as shown in FIG. 5, for example.

Also, this video signal is inputted to the diaphragm control circuit 26, and this diaphragm control circuit 26 calculates average brightness by integrating a luminance signal component of this video signal by a predetermined cycle or the like. Also, this diaphragm control circuit 26 applies a signal of a difference obtained by subtracting a reference value corresponding to appropriate brightness from this average brightness signal to the diaphragm 23 as a diaphragm control signal so as to adjust an opening amount of this diaphragm 23. And light is automatically controlled so that the illumination light amount passing through the diaphragm 23 becomes a reference value.

As shown in FIG. 2, a channel 38 for inserting of treatment instrument is provided inside the insertion portion 11, and the rear end side of this treatment instrument channel 38 communicates with an insertion port 39 for treatment instrument provided in the vicinity of the front end of the operation portion 12.

Also, in this insertion portion 11, UPD coils 41 are arranged with a predetermined interval, for example, and a signal line 42 connected to the UPD coil 41 is connected to an UPD coil driving circuit 43 provided inside the video processor 6 through an electric contact of the connector 14 as shown in FIG. 1.

This UPD coil driving circuit 43 sequentially applies an AC driving signal to each of the UPD coils 41 via the signal line 42 so as to generate an AC magnetic field around each of the UPD coils 41.

Also, at a predetermined position around a bed on which a patient, not shown, lies, into which the insertion portion 11 is inserted, an UPD coil unit 7 made from a plurality of UPD coils 44 is arranged. And by the plurality of UPD coils 44, a magnetic field generated by the UPD coils 41 arranged inside the insertion portion 11 is detected.

A detection signal by the UPD coil 44 is amplified by an amplifier 45 inside the UPD device 8 and then, inputted to an UPD coil-position calculation circuit 46. And this UPD coil-position calculation circuit 46 calculates a position of each of the UPD coils 41 from an amplitude value and a phase value in a signal detected by the UPD coil 44.

The position information calculated by this UPD coil-position calculation circuit 46 is inputted to an insertion-shape calculation/display processing circuit 47. The insertion-shape calculation/display processing circuit 47 executes processing for estimating an insertion shape of the insertion portion 11 from the shape coupling the calculated position of each of the UPD coils 41 and signal processing for display as an UPD image Ib by modeling the estimated insertion shape.

The video signal of the UPD image Ib outputted form this insertion-shape calculation/display processing circuit 47 is inputted to the high-definition monitor 10 through the image mixer 9, and the UPD image Ib is displayed on the display screen as shown in the right side in the screen in FIG. 5, for example.

Information of the UPD image Ib outputted from the insertion-shape calculation/display processing circuit 47 is also inputted to a supplementary image generation circuit 48. This supplementary image generation circuit 48 generates a corresponding image of the shape in the body cavity from the information of the inputted UPD image Ib as a supplementary image. And a video signal of this supplementary image is outputted to the image mixer 9, and the image mixer 9 superimposes this supplementary image on the UPD image Ib and outputs it to the high-definition monitor 10.

In the UPD image Ib in the right on the screen in FIG. 5, an actual UPD image is shown by reference character Ib', and a supplementary image such as a corresponding digestive duct is shown by reference character Ib". That is, a normal UPD image is shown by the reference character Ib', and in this embodiment, the supplementary image generation circuit 48 generates the supplementary image Ib" in the outline shape in the body cavity into which the corresponding insertion portion 11 is actually inserted from information of the UPD image Ib'. And the UPD image Ib' and the supplementary image Ib" are displayed on the high-definition monitor 10 at the same time.

This supplementary image Ib" is generated by reading a supplementary image corresponding to the actual UPD information Ib' from information on a digestive duct or the like organized in a database. And this supplementary image Ib" is superimposed on the UPD image Ib' as shown in FIG. 5 for display. The reference character Ib is used below merely as an UPD image.

As shown in FIG. 2, the UPD coil 41 is also mounted inside the insertion portion 15. Specifically, at the distal end portion 15, two UPD coils 41 are arranged while being separated along a direction crossing the longitudinal direction of the insertion portion (vertically, for example).

The UPD coil-position calculation circuit 46 calculates a position of the distal end portion 15 from the positions of the two UPD coils 41, for example, mounted at the distal end portion 15 as well as a circumferential direction around the axial direction of the distal end portion 15 (particular direction in a direction such as vertical or horizontal). The UPD coil-position calculation circuit 46 also detects information in the longitudinal direction (axial direction) around the distal end portion 15, which is utilized at display.

The information of the position and direction (axial direction and circumferential direction) is outputted to the bending control device 5. The bending control device 5 can detect knowledge on which direction the distal end portion 15 is actually oriented.

Also, the insertion-shape calculation/display processing circuit (CPU calculation/display processing circuit) 47 outputs information on display direction (viewpoint direction for display) when the UPD image Ib is displayed to the bending control device 5. This information on display direction includes information in the axial direction of the distal end side of the insertion portion 11 in the UPD image Ib. In this embodiment, an example is described that the axial direction of the insertion portion at the distal end side is oriented substantially upward on the display screen when the UPD image Ib is displayed for simplification.

Also, the bending control device 5 performs normal bending control when a bending control mode (hereinafter abbreviated as bending mode) corresponding to an endoscopic image Ia is selected by the bending-mode selection switch 19 (selection portion).

On the other hand, when the bending mode corresponding to the UPD image Ib is selected by the bending-mode selection switch 19, the bending control device 5 changes the content of the bending control so that the bending control corresponding to the UPD image Ib is executed. That is, the bending control device 5 of the present invention is provided with a function to perform two types of bending control (two bending control means or two bending control methods) different from each other corresponding to each of the two images Ia, Ib, which are different from each other.

Also, in this embodiment, an index indicating which bending mode has been selected is displayed in the endoscopic image Ia or the UPD image Ib. For example, when the bending mode corresponding to the UPD image Ib is selected, an index E reading Angle is displayed in the UPD image Ib on the right side in FIG. 5 so as to facilitate understanding by the operator.

That is, in FIG. 1, the selection signal of the bending mode from the bending-mode selection switch 19 is inputted to the bending control device 5 and also inputted to the video processing circuit 37 for displaying the index E from the selection signal, and the video processing circuit 37 displays the index E reading Angle, for example, corresponding to the selected state of the bending mode in the endoscopic image Ia or in the UPD image Ib.

Figure 3:
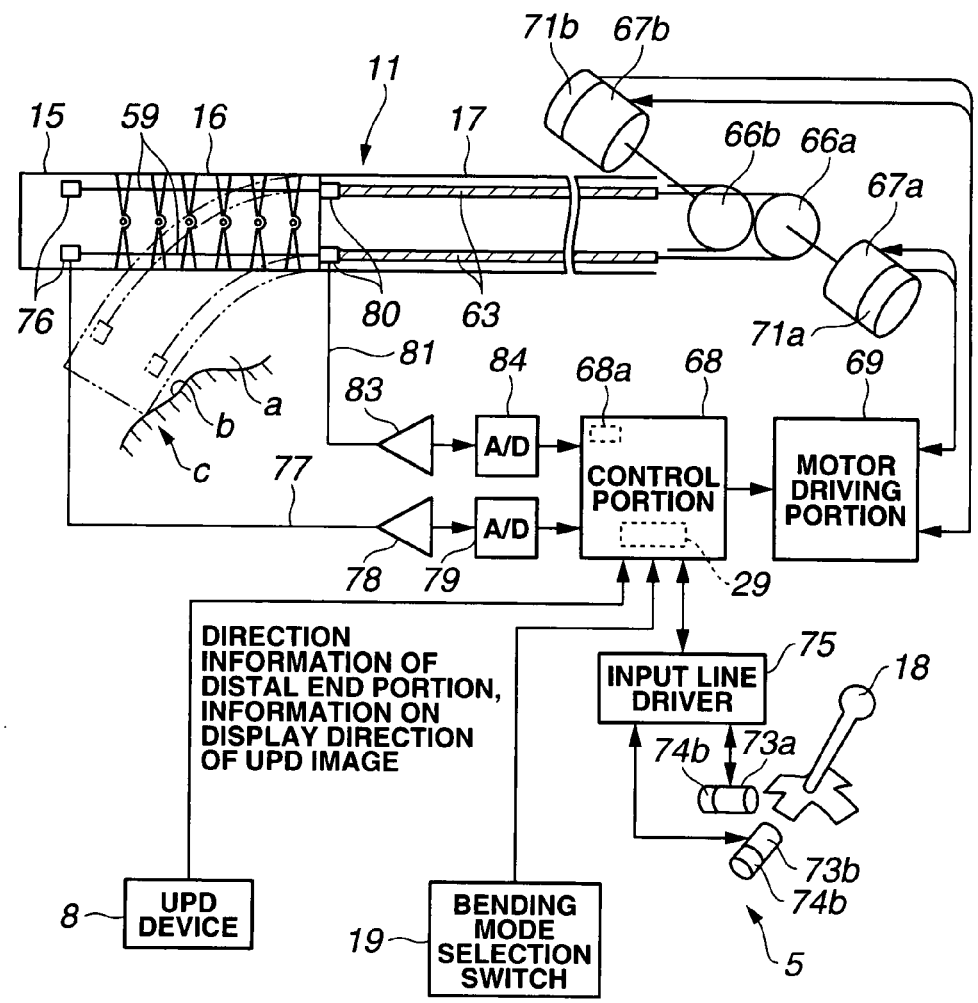
FIG. 3 is a block diagram showing a configuration of a bending control device of the first embodiment.
Figure 4:
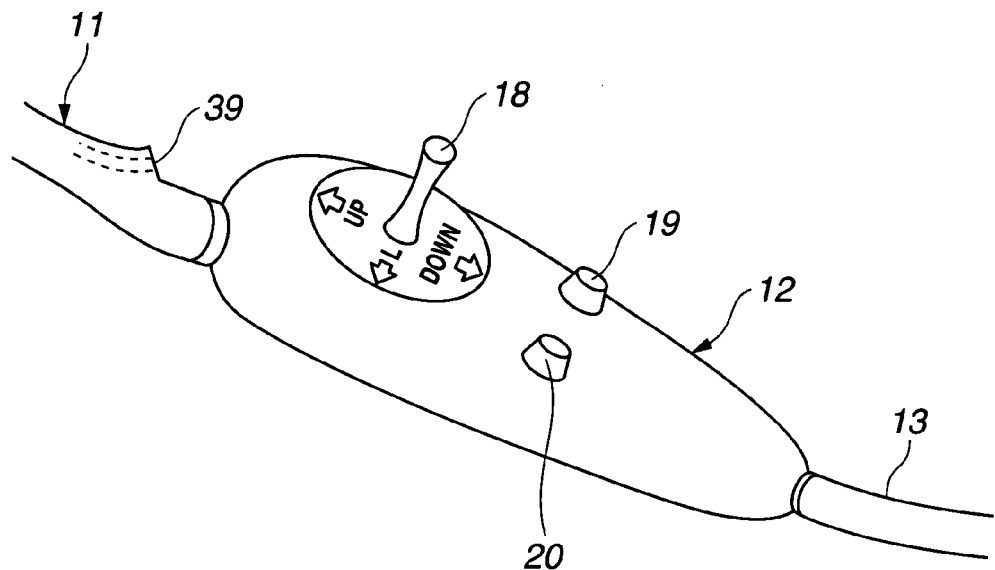
FIG. 4 is an appearance view showing a configuration of the periphery of an operation portion.

In the insertion portion 11 of the endoscope 2 in this embodiment, the bending portion 16 as shown in FIG. 2 is provided, and the bending control device 5 for executing bending control of this bending portion 16 is in the construction as shown in FIG. 3. As shown in FIG. 2, the flexible tube portion 17 has a helical tube 51 fitted with a braided tube 52 and the outside covered by an envelope 53. The helical tube 51 is formed in the cylindrical shape by wrapping a strip-state metal plate, while the braided tube 52 is formed in the cylindrical shape by braiding a large number of metal wires.

Also, the bending portion 16 has a plurality of bending pieces 54 arranged in the longitudinal axis direction of the insertion portion 11, and by rotatably installing the adjacent bending pieces 54 consecutively to each other by rivets 55, a tubular bending tube portion 56 which can be freely bent in the longitudinal direction is constructed. The outer circumference of this bending tube portion 56 is fitted with a cylindrical braid and its outer circumference is covered by an envelope 58.

The bending direction of each of the bending pieces 54 is determined by the position to install the rivet 55, but the rivet 55 here is arranged alternately at a horizontal direction and a vertical direction or at an appropriate interval so that the entire bending tube portion 56 can be bent horizontally and vertically. And the bending tube portion 56 constitutes a bending mechanism 60 which is bent in a direction pulled by an angle wire 59.

Also, on the inner surface of the other bending pieces 54 except the bending piece 54 located at the leading end and the bending piece 54 located at the trailing end, ring-state wire guides 61 through which each angle wire 59 is individually inserted to be guided capable of advance/retreat are mounted by brazing or the like at positions corresponding to the angle wires 59 arranged at up and down as well as right and left positions.

The distal end of each angle wire 59 is fixed by brazing or the like to the bending piece at the leading end or the body member of the distal end portion 15. Then, by selecting any of the angle wires 59 and pulling it, the bending portion 16 can be bent in the direction of the selected angle wire 59.

The flexible tube portion 17 and the bending portion 16 of the insertion portion 11 are connected to each other by a metal connection tube 62. The laminated distal end portions of the helical tube 51 and the braid tube 52 in the flexible tube portion 17 are fitted in the rear end portion of the connection tube 62 and fixed by brazing or the like. Also, the rear end of the bending piece 54 located at the last in the bending tube portion 56 in the bending portion 16 is fitted with the outer circumference of the distal end portion of the connection tube 62 and fixed by brazing, screwing or the like.

The rear end portion of the braid and the envelope 58 of the bending portion 16 exceeds the bending piece 54 located at the last end and reaches the outer circumference portion of the connection tube 62, covers the outer circumference of the connection tube 62 and fixed thereto by brazing or the like.

The envelope 53 of the flexible tube portion 17 and the envelope 58 of the bending portion 16 are abutted to each other, and the outer circumference portion over the both ends of the abutment is fastened by a thread winding portion wound tightly, and the abutment portion is sealed in the liquid tight manner by applying an adhesive on the outer circumference of this thread winding portion. And the connection portion between the flexible tube portion 17 and the bending portion 16 is a relatively rigid area.

Each angle wire 59 is individually inserted through respective guide sheath 63 in the flexible tube portion 17 and guided to the operation portion 12.

This guide sheath 63 comprises, for example, a coil sheath formed by winding a coil wire made of stainless steel (SUS) tightly in the coil state, and the respective angle wire 59 is inserted through each coil sheath.

The distal end of the coil sheath is fixedly mounted to the inner surface of the connection tube 62 by brazing. The rear end side of the coil sheath is arranged in the free state inside the flexible tube portion 17 of the insertion portion 11 and guided into the operation portion 12 together with those incorporated.

On the other hand, as shown in FIG. 3, a pulley 66a around which a wire with each of the upper and lower angle wires 59 connected to the both ends is wound and a pulley 66b around which a wire with each of the right and left angle wires 59 connected to the both ends is wound are arranged in the operation portion 12.

The pulleys 66a, 66b can be rotated forward/backward by electric motors 67a, 67b. The electric motors 67a, 67b are driven by a motor driving portion 69 controlled by a control portion 68.

The pulleys 66a, 66b are rotated by the electric motors 67a, 67b, and an actuator for bending-control of the bending portion 16 is constituted through the angle wires 59.

The driving position of the actuator is detected by actuator position detecting means. The actuator position detecting means here comprises rotary encoders 71a, 71b mounted at shaft portions of the electric motors 67a, 67b, and a bending angle of the bending mechanism 60 is detected on the basis of an output signal of the rotary encoders 71a, 71b.

The control portion 68 controls a bending operation amount by the actuator on the basis of a position detection signal of the actuator position detecting means so as to bend the bending portion 16 to a predetermined bending angle.

That is, the joystick 18 as bending instruction operation means is provided at the operation portion 12. By this joystick 18, an arbitrary vertical, horizontal bending direction is instructed and an instruction on the bending operation amount (bending angle) is given.

By giving an instruction of the bending direction such as up, down, right or left and an instruction of the bending operation amount, a vertical-direction joystick motor 73a and a horizontal-direction joystick motor 73b are rotated. The rotating angle, that is, the bending operation amount is detected by the rotary encoders 74a, 74b, and detection signals of the rotary encoders 74a, 74b are inputted to the control portion 68 through an input driver 75.

Next, means for detecting the state of the bending portion 16 will be described.

As shown in FIG. 2, at the distal end portion 15 of the insertion portion 11, a tension sensor 76 such as a strain sensor is fixed corresponding to each angle wire 59, and to this tension sensor 76, the distal end portion of the angle wire 59 is connected so as to detect tension of the angle wire 59.

A signal line 77 of the tension sensor 76 is connected to a tension sensor amplifier 78 inside the operation portion 2 through the insertion portion 11 and to the control portion 68 through an A/D converter 79.

Moreover, inside the connection tube 62 between the distal end portion of the flexible tube portion 17 and the rear end portion of the bending portion 16, a displacement sensor 80 such as a magnetic induction sensor, laser displacement sensor and the like is fixed corresponding to the angle wire 59 so as to detect a displacement amount in the axial direction of the angle wire 59.

The displacement sensor 80 is incorporated in a coil sheath portion for insertion guiding of the angle wire 59. To the displacement sensor 80, a signal line 81 is connected, and this signal line 81 is connected to a displacement sensor amplifier 83 inside the operation portion 12 through the insertion portion 11 and to the control portion 68 through an A/D converter 84.

When an external force is not applied to the bending portion 16, a relation between tension measured by the tension sensor 76 and displacement measured by the displacement sensor 80 shows, as in a certain bend, rise of tension against the displacement. However, the relation between the tension observed when the bending portion 16 is bent or measured by the tension sensor during procedure and the displacement measured by the displacement sensor 80 falls out of characteristics indicated when the external force is not applied.

As shown in FIG. 3, when the insertion portion 11 is inserted into a digestive duct a, for example, and the bending portion 16 is bent, the displacement amount of the angle wire 59 is measured by the displacement sensor 80, and the measurement result is inputted to the control portion 68 through the displacement sensor amplifier 83 and the A/D converter 84.

Also, when the bending portion 16 is bent, when the distal end portion 16 hits a tube wall b and the bending portion 16 is further bent, or when an external force is applied from the tube wall b in the arrow c direction, the tension is measured by the tension sensor 76, and the measurement result is inputted to the control portion 68 through the tension sensor amplifier 78 and the A/D converter 79.

In the normal bending mode, the control portion 68 calculates a difference in tension and operates the input driver 75 so as to feedback a force amount with the size of the difference to the joystick 18. Therefore, the fact that the distal end portion 15 receives the external force can be known by feeling of a hand of the operator operating the joystick 18.

In this way, by installing the displacement sensor 80 for measuring the displacement amount of the angle wire 59 in the insertion portion 11, even if the shape of the insertion portion 11 is changed, control to overcome so-called angle down can be surely performed. Also, by installing the tension sensor 76 for measuring the tension of the angle wire 59, when the bending portion 16 is bent and the distal end portion 15 hits the tube wall b or the like and receives the external force c, the tension is measured by the tension sensor 76.

By calculating the difference in tension by the control portion 68 and feeding back the force amount with the size of the tension difference to the joystick 18, the fact that the distal end portion 15 receives the external force is known by the feeling of a hand of the operator operating the joystick 18. Then, operation such as returning the bending of the bending portion 16 to the original state by the joystick 18 or change of the bending direction can be made, which improves operability.

Also, in this embodiment, the bending control device 5 is capable of bending control in a bending mode (second bending mode) corresponding to the UPD image Ib other than the normal bending mode (first bending mode) for bending control corresponding to the normal endoscopic image Ia.

In this case, the relation between the endoscopic image Ia in the normal bending mode and the bending direction of the bending portion 16 or the joystick 18 is as follows.

The CCD 33 is fixed inside the distal end portion 15 and the up direction of an image captured by the CCD 33 matches a predetermined bending direction of the bending portion 16, the up bending direction, for example. Also, when an image captured by the CCD 33 is signal-processed and displayed as the endoscopic image Ia on the high-definition monitor 10 as the image display device, it is displayed on the high-definition monitor 10 with the up direction of this endoscopic image Ia oriented upward all the time. In this case, the other directions of the endoscopic image Ia in the high-definition monitor 10, that is, the down and the right and left directions are also displayed in the fixed state. And when one bending direction in the bending portion 16 or the joystick 18 matches one direction in the endoscopic image Ia, all the directions correspond respectively. This is also a publicly known function realized by existing endoscope devices.

On the other hand, in a second bending mode to be the characteristic of this embodiment, the UPD image Ib is associated with the bending portion 16 or the joystick 18 in a predetermined relation so that the operator can give a bending instruction operation while looking at the UPD image Ib.

Therefore, as mentioned above, the control portion 68 of the bending control device 5 takes in the direction information of the distal end portion 15 by the UPD device 8 and the information on display direction (of the UPD image Ib) with a predetermined time interval and stores them in an internal memory or the like.

As described later, a direction correction circuit 29 provided inside the control portion 68 calculates a direction discrepancy amount (angle of direction discrepancy) on how far a predetermined direction of the distal end portion 15 in the UPD image Ib (specifically, up and down as well as right and left directions of a portion displayed in the display image of the distal end portion 15) is displaced from the actual direction as a direction correction amount.

Also, in this bending mode, the axial direction of the distal end portion 15 in the UPD image Ib (this axis is not changed with respect to axial rotation of the distal end portion 15 as will be described later) is associated with the predetermined direction of the bending portion 16 or the joystick 18 in operation (so as to facilitate operation of the both). That is, the bending instruction direction determined by looking at the UPD image Ib is associated with the bending instruction direction by the joystick 18 as bending instruction operation means for bending instruction operation of the bending portion 16. Specifically, when the UPD image Ib is to be displayed, the axial direction of the distal end portion 15 is displayed as the vertical direction all the time, for example, and the distal end side of the distal end portion 15 is oriented upward.

Also, the vertical direction by the joystick 18 is defined, and when the joystick 18 is operated, the direction of operation instruction by the joystick 18 is corrected by a discrepancy amount calculated by the direction correction circuit 29 so as to bend and drive the bending portion 16.

By this construction, in the second bending mode by the UPD image Ib, it is only necessary for the operator to look at the UPD image Ib and to give bending instruction operation of tilting the joystick 18 in the direction to bend the bending portion 16 from the UPD image Ib. The control portion 68 executes bending control according to the inclined operation of the joystick 18 in the publicly known manner in the normal bending mode, but when the second bending mode corresponding to the UPD image Ib is selected, the bending control is made using the inclined direction of the joystick 18 corrected by the direction correction circuit 29 inside the control portion 68.

Therefore, when the operator such as a practitioner looks at the UPD image Ib and merely operates the joystick 18 in the direction to bend, the bending control device 5 executes controlling bending of the bending portion 16 in the direction to which bending is desired in the UPD image Ib.

Action of this embodiment according to the above configuration will be described specifically.

Figure 6:
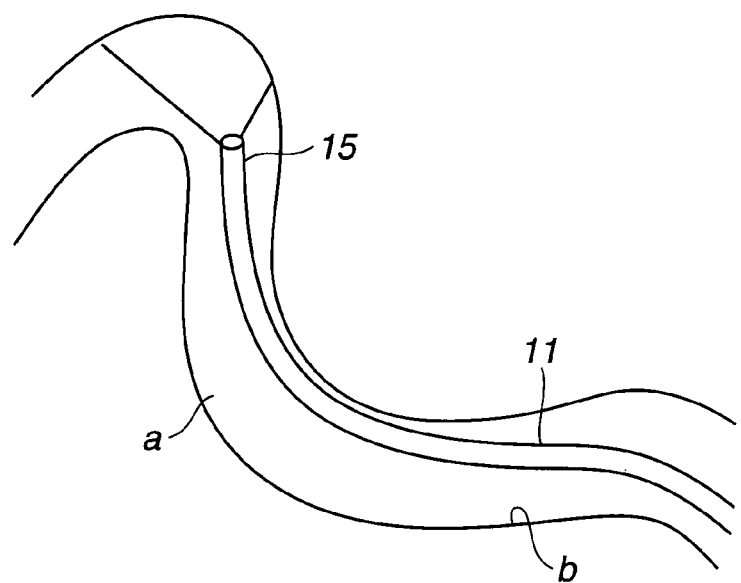
FIG. 6 is a view showing a state of an insertion portion of the endoscope inserted into a body cavity.

The connector 14 of the endoscope 2 is connected to the video processor 6 as shown in FIG. 1, and the insertion portion 11 of the endoscope 2 is inserted into a bent digestive duct a of the patient, for example. The state where the insertion portion 11 is inserted into the digestive duct a is shown in FIG. 6.

Figure 7:
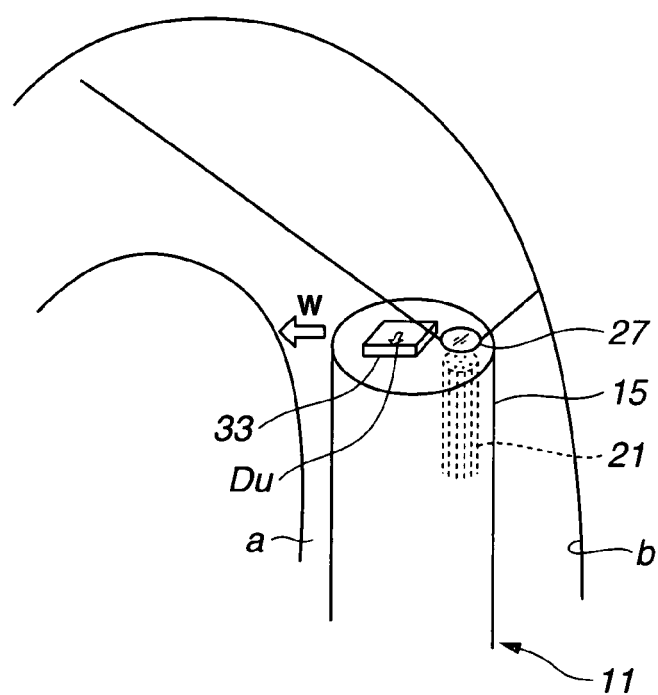
FIG. 7 is an enlarged outline view showing the vicinity of a distal end portion in FIG. 6.

Also, an enlarged outline view around the distal end portion 15 in this state is shown in FIG. 7. In FIG. 7, actually, the objective lens 32 is arranged in front of the CCD 33, but it is omitted for simplification.

As shown in FIG. 7, the up direction of the CCD 33 incorporated in the distal end portion 15 is supposed to be a direction shown by an arrow Du, for example. Also, in FIG. 7, the digestive duct a is bent to the left side, and thus, by pushing in the insertion portion 11 by bending the bending portion 16 in the direction shown by an arrow W, the insertion portion 11 can be smoothly inserted into the deep side of the bent digestive duct a (as will be described later, in the UPD image Ib, the bending instruction operation to bend in this way is given).

Figure 8:
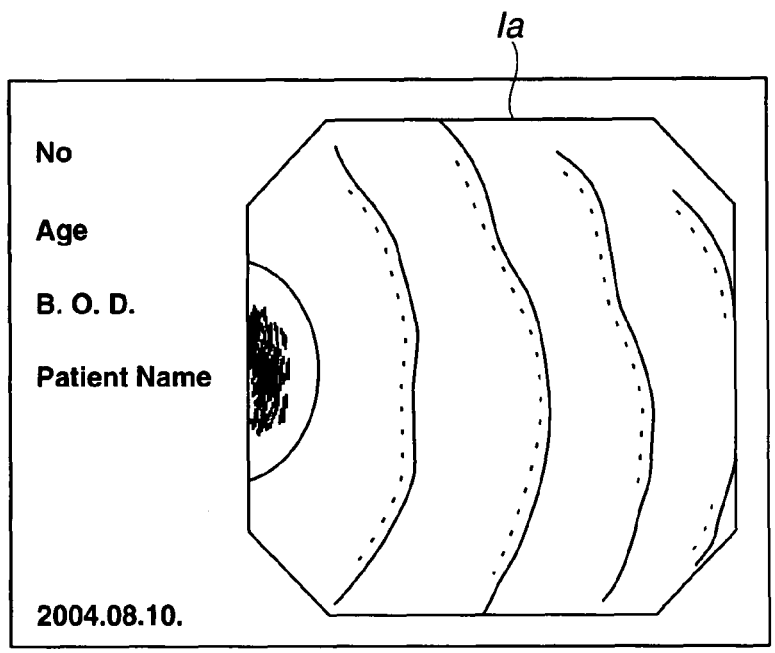
FIG. 8 is a diagram showing an endoscopic image in the insertion state in FIG. 7.

As with this case, when the up direction of the CCD 33 is the direction shown by the arrow Du, the endoscopic image Ia captured by the CCD 33 is as shown in FIG. 8. The endoscopic image Ia shows the up direction in the CCD 33 upward all the time.

As shown in FIG. 8, in the displayed endoscopic image Ia, a dark portion in the digestive duct a corresponds to the direction of the lumen (the reflected light from the direction along the lumen is weakened and thus, the image in the traveling direction of the lumen becomes dark).

Therefore, when the operator is to insert the distal end portion 15 of the insertion portion 11 smoothly into the deep side of the bent digestive duct a while observing the endoscopic image Ia as shown in FIG. 8, the operator should tilt the joystick 18 in the left direction in order to bend the bending portion 16 to the left side where a dark image portion exists.

Also, when the insertion portion 11 is to be inserted into a bent body cavity in general, the operator often performs operation such as twisting the insertion portion 11 in order to smooth the insertion.

Figure 9:
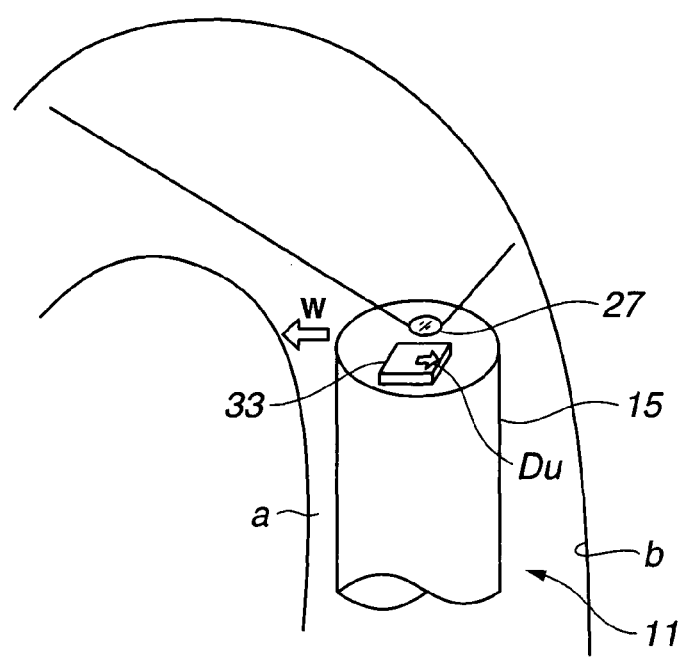
FIG. 9 is a view showing a state where the distal end portion of the insertion portion in FIG. 7 is rotated clockwise by 90°.

For example, in FIG. 7, suppose that the insertion portion 11 is twisted clockwise by 90 degrees and the up direction of the CCD 33 is oriented to the right direction shown by the arrow Du as shown in FIG. 9. The endoscopic image Ia taken by the CCD 33 in this state is as shown in FIG. 10.

Figure 10:
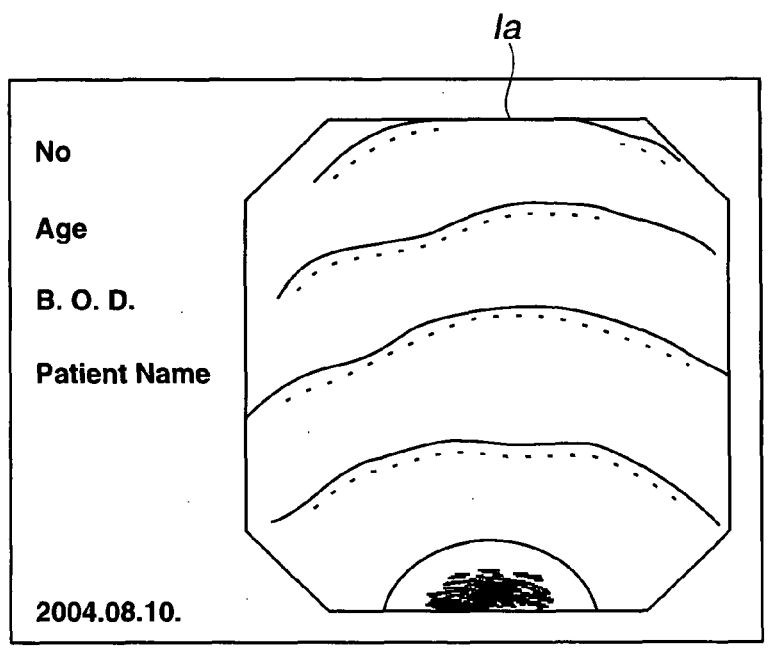
FIG. 10 is a diagram showing an endoscopic image in the insertion state in FIG. 9.

FIG. 10 is an image obtained by rotating the endoscopic image Ia in FIG. 8 by 90°. And when the distal end portion 15 of the insertion portion 11 is to be smoothly inserted into the digestive duct a while observing this endoscopic image Ia, the operator should tilt the joystick 18 downward in order to bend the bending portion 16 to the lower side where the dark image portion exists.

Also, in the case of the insertion state shown in FIG. 9, the operator can smoothly insert the bending portion 16 into the deep side in the bent digestive duct a by bending and inserting the bending portion 16 in the direction shown by the arrow W.

Figure 11:
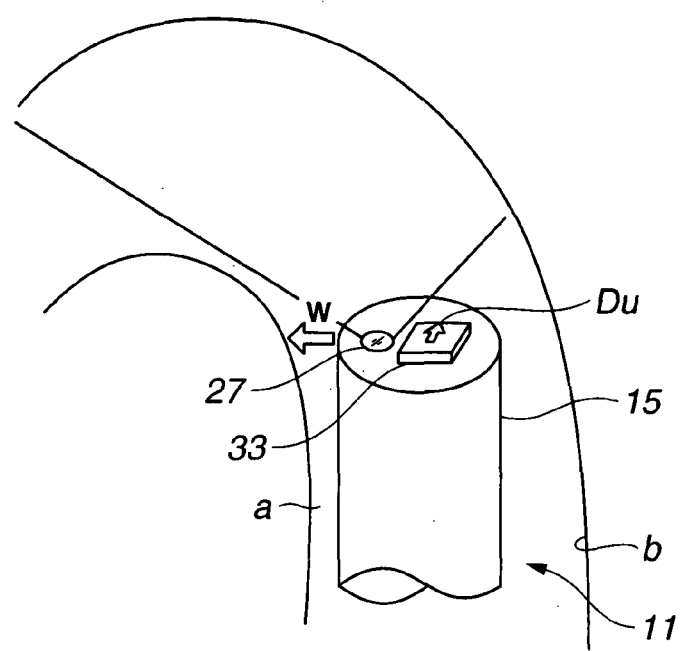
FIG. 11 is a view showing a state where the distal end portion of the insertion portion in FIG. 9 is further rotated clockwise by 90°.

Moreover, in FIG. 9, suppose that the insertion portion 11 is twisted clockwise by 90 degrees and the up direction of the CCD 33 as shown in FIG. 11 is oriented to the down direction on the drawing as shown by the arrow Du.

In this state, too, by performing the same operation as that mentioned above by observing the corresponding endoscopic image Ia, not shown, smooth insertion into the deep side of the digestive duct a can be realized easily. Also, in the insertion state shown in FIG. 11, when the operator bends and inserts the bending portion 16 in the direction shown by the arrow W, smooth insertion into the deep side of the bent digestive duct a can be realized. On the other hand, there might be a case that the direction of the lumen is hardly known from the endoscopic image Ia such that the distal end portion 15 gets too close to the wall surface of the digestive duct a, for example.

In that case, the operator may set the bending mode corresponding to the UPD image Ib by operating the bending-mode selection switch 19.

The UPD image Ib is displayed as shown in the right side on the screen in FIG. 5. In this case, it was not known in the conventional example to which state shown in FIGS. 7, 9, 11 or the like the state of the distal end portion 15 of the insertion portion 11 corresponds. On the other hand, the control portion 68 can grasp the relation between the predetermined direction of the distal end portion 15 in the UPD image Ib in FIG. 5 and the actual direction of the distal end portion 15 (or the bending direction of the joystick 18) by taking in the direction information of the distal end portion 15 by the UPD coils 41 and the information on display direction to actually display the UPD image Ib.

In this embodiment, the predetermined direction in the image of the distal end portion 15 in the UPD image Ib is associated in operation with the predetermined bending direction of the joystick 18 so that the bending control can be made considering discrepancy in the directions of the both at actual bending driving.

Specifically, in the up and down as well as the right and left direction around the axis faced to the distal end side along the axis of the distal end portion 15 in the UPD image Ib, the up direction perpendicular to the drawing surface is made to match the up direction of the bending instruction of the joystick 18 in operation, for example. Moreover, the display direction of the UPD image Ib is set so that the axial direction around the distal end portion in the UPD image Ib is oriented close to the up direction on the display screen.

In any of the FIGS. 7, 9 and 11, by setting the up direction perpendicular to the drawing surface to the up direction in the bending instruction of the joystick 18, by pushing-in operation of the insertion portion 11 by the operator while tilting the joystick 18 in the left direction, the control portion 68 corrects the directional discrepancy from the actual up direction of the bending portion 16 by the direction correction circuit 29 corresponding to the tilting operation in the left direction and controls bending driving so that the bending portion 16 is bent in the direction instructed in the UPD image Ib in any of FIGS. 7, 9 and 11.

For example, in the case of FIG. 7, direction correction by the direction correction circuit 29 is not executed. On the other hand, in the case of FIG. 9, the control portion 68 executes bending control by direction correction by the direction correction circuit 29 as if the bending instruction to the down direction is actually given when the bending to the left direction is instructed.

In this case, for the other directions, when the bending to the down direction is instructed, the direction correction is made as if the bending instruction to the right direction is actually given, when the bending to the right direction is instructed, the direction correction is made as if the bending instruction to the up direction is given, and when the bending to the up direction is instructed, the direction correction is made as if the bending instruction to the left direction is actually given.

In operation, in this way, it is only necessary for the operator to bend the joystick 18 in the direction desired to bend the bending portion 16 at the base end of the distal end portion 15 in the UPD image Ib, even if the bending direction of the bending portion 16 does not actually match the direction, the bending portion 16 can be bent in the desired bending direction in the UPD image Ib by direction correction by the direction correction circuit 29 in the control portion 68.

Figure 12:
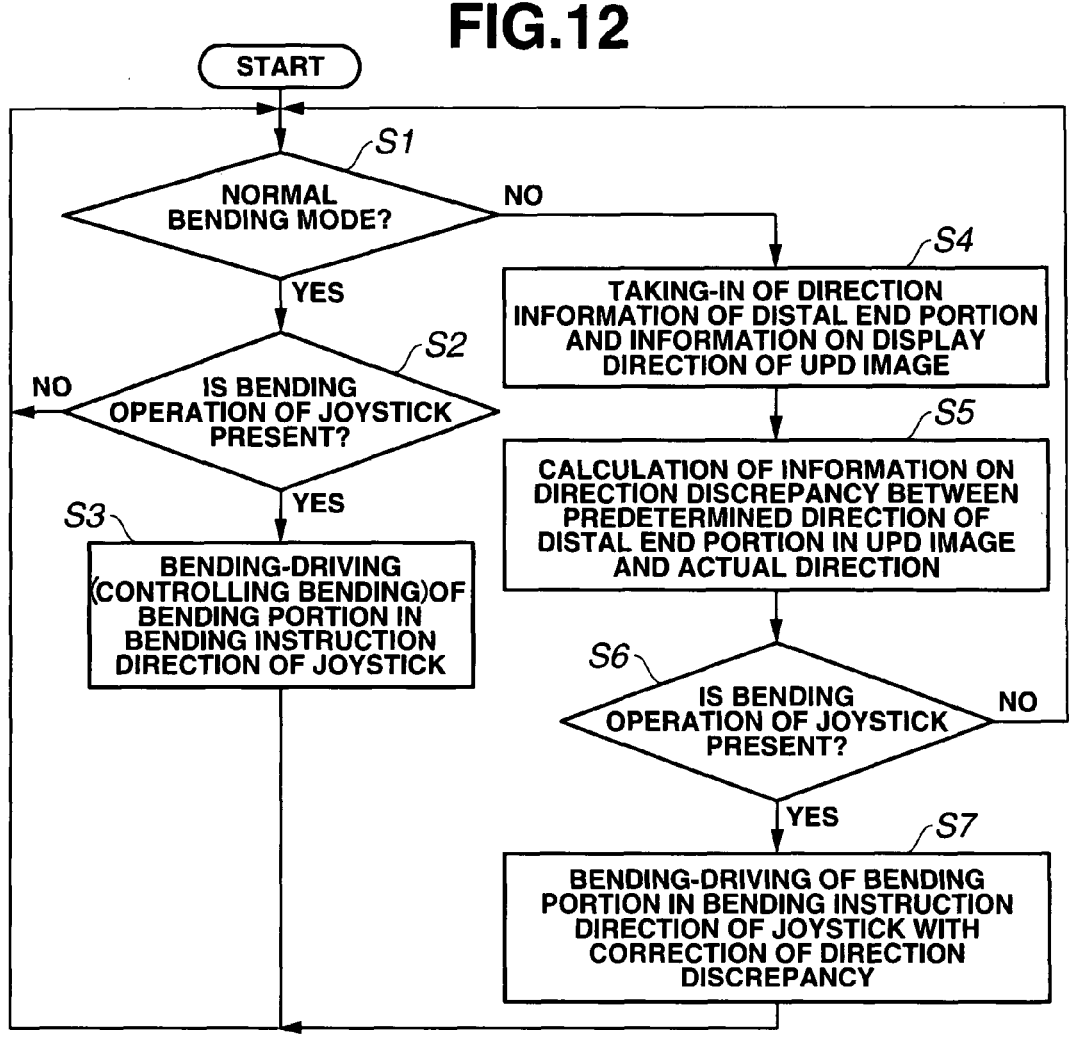
FIG. 12 is a flowchart showing a procedure of bending control in the first embodiment.

FIG. 12 shows an outline operation content of this embodiment. In the state as set in FIG. 1, the insertion portion 11 of the endoscope 2 is inserted into digestive duct a and the like. A CPU 68a constituting the control portion 68 of the bending control device 5 is, as shown in Step S1, determines if the normal bending mode has been selected by the bending mode selection switch 19.

When the normal bending mode has been selected, the CPU 68a of the control portion 68 determines, as shown in Step S2, if the joystick 18 has been operated for bending or not. If there has been no bending operation, the routine goes back to Step S1.

If there is a bending operation, as shown in Step S3, the CPU 68a drives the electric motor 67a or 67b so as to bend the bending portion 16 in the bending instruction direction of the joystick 18. And the routine goes back to Step S1.

At Step S1, when not in the normal bending mode, it is set in the bending mode corresponding to the UPD image Ib. Thus, as shown in Step S4, the CPU 68a takes in the direction information of the distal end portion 15 and the information on the display direction of the UPD image Ib.

At the subsequent Step S5, the CPU 68a calculates information (angle) on direction discrepancy between the predetermined direction of the distal end portion in the UPD image Ib and the actual direction.

Also, the CPU 58a determines if there is bending operation of the joystick 18 at the subsequent Step S6. If there is no bending operation, the routine goes back to Step S1.

If there is a bending operation, as shown in Step S7, the CPU 68a makes correction of the direction discrepancy for the bending instruction direction of the joystick 18 and drives the electric motor 67a or 67b so as to bend the bending portion 16. And the routine goes back to Step S1.

In FIG. 12, Steps S4 and S5 may be executed after Step S6. Since each Step is carried out in a short time in a closed loop manner, the operation would be substantially the same even if the order is changed.

This embodiment having the above action has the following effects.

According to this embodiment, the operator can perform work such as insertion more smoothly than before by setting the bending mode corresponding to the image for which the bending operation can be carried out easily in two images Ia, Ib shown in FIG. 5.

If bending is to be done in the bending mode corresponding to the endoscopic image Ia as shown in FIG. 5, for example, when bending operation is made by the joystick 18, a direction indication portion such as a marker Ma, Mb or the like may be displayed in the endoscopic image Ia to show the direction to which bending is to be made by the bending operation. In this way, the operator can carry out bending more easily.

Also, if bending is to be done similarly in the bending mode corresponding to the UPD image Ib, when bending operation is made by the joystick 18, the direction indication portion such as a marker Mc, Md or the like may be displayed in the UPD image Ib to show the direction to which bending is made by the bending operation. In this way, the operator can carry out bending more easily.

The direction to be a reference in bending operation by the joystick 18 in the UPD image Ib shown in FIG. 5, that is, the up, left or right direction may be displayed by a marker or an arrow, for example.

If the UPD image Ib is to be displayed, the UPD image may be displayed in a designated display direction so as to display the UPD image in the designated display direction or a plate for designating the display direction may be used. If a display method where the longitudinal direction of the distal end portion 15 is a display surface (included in the display surface) is employed, the bending direction instruction and bending control or the like corresponding to the bending instruction may be given more accurately.

The UPD image Ib displayed for a case where the axial direction of the distal end side of the insertion portion 11 extends substantially in the up direction as shown in the right side in FIG. 5 has been described, but display may be made so that the axial direction of the distal end portion of the insertion portion 11 extends in a different direction.

For example, if the UPD image Ib is rotated counterclockwise from the displayed state in FIG. 5 by about 90 degrees so as to display the UPD image Ib so that the axial direction of the distal end portion of the insertion portion 11 extends to the left side, it is only necessary to execute bending control considering the case where the display direction is set in the direction displaced by 90 degrees in actual bending driving.

As the direction to which the distal end side of the insertion portion 11 extends in the UPD image Ib, a direction closer to any of the up, down, right or left direction is more preferable than the other intermediate directions since determination of the direction can be made more easily when determining the bending instructing direction by looking at this UPD image Ib.

In the first embodiment, the configuration for displaying the insertion shape of the insertion portion 11 using the UPD coil 41 and the like was described, but at least the position or direction of the distal end side of the insertion portion 11 may be detected using the other position detecting means. For example, a high-frequency IC tag (RF tag) can be used to detect the direction of the vicinity of the distal end portion 15 and to display an image of the vicinity of the distal end portion 15.

When the control portion 68 constituting the bending control device 5 shown in FIG. 5 by the CPU 68a and the like, the processing content shown in FIG. 12 may be executed by the CPU 68a in the software manner according to a program stored in the memory or the like.

Also, a bending control method for carrying out bending control along the processing content shown in FIG. 12 may be employed. In the above-mentioned first embodiment, each image of the video processor 6 and the UPD device 8 is mixed by the image mixer 9 and outputted to the high-definition monitor 10 at the same time, but one of them may be selected and displayed.

Figure 13:
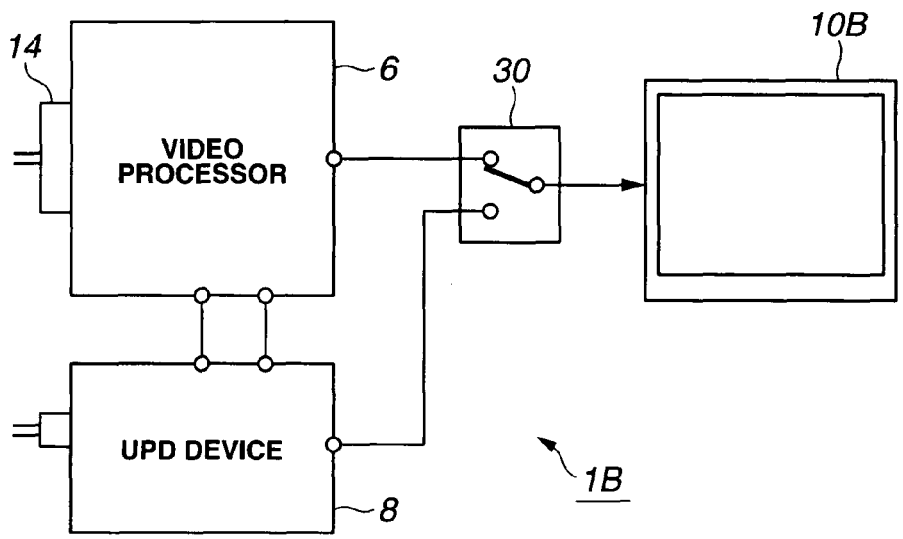
FIG. 13 is a block diagram showing a part of the configuration of an endoscope device of a first variation.

Also, as in an endoscope device 1B of a first variation shown in FIG. 13, each image of the video processor 6 and the UPD device 8 may be selected and outputted to a monitor 10B through a switch 30.

Figure 14:
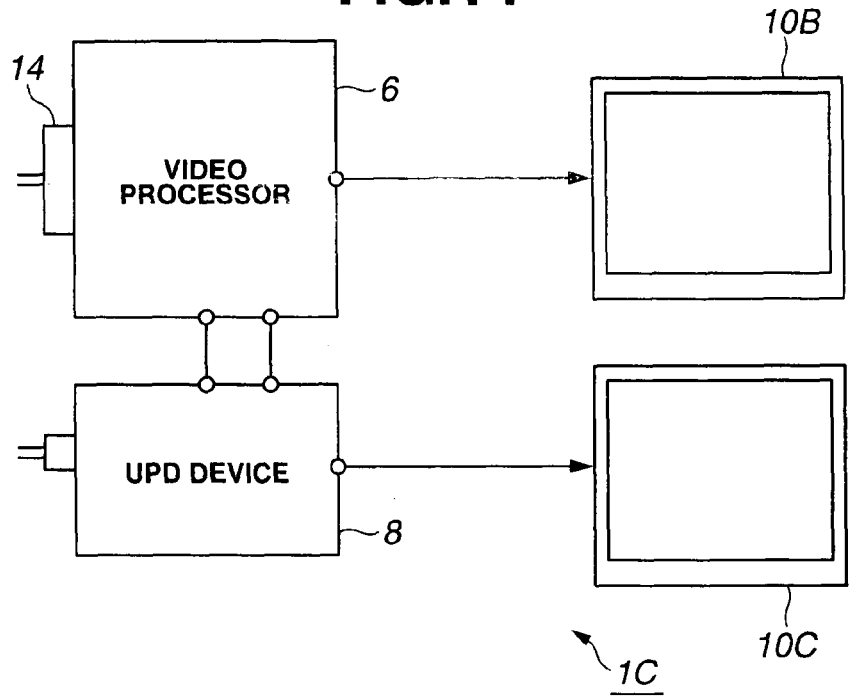
FIG. 14 is a block diagram showing a part of the configuration of an endoscope device of a second variation.

Also, as in an endoscope device 1C of a second variation shown in FIG. 14, each image of the video processor 6 and the UPD device 8 may be displayed on separate monitors 10B and 10C, respectively.

Next, a third variation of this embodiment will be described referring to FIGS. 15A and 15B.

Figure 15A:
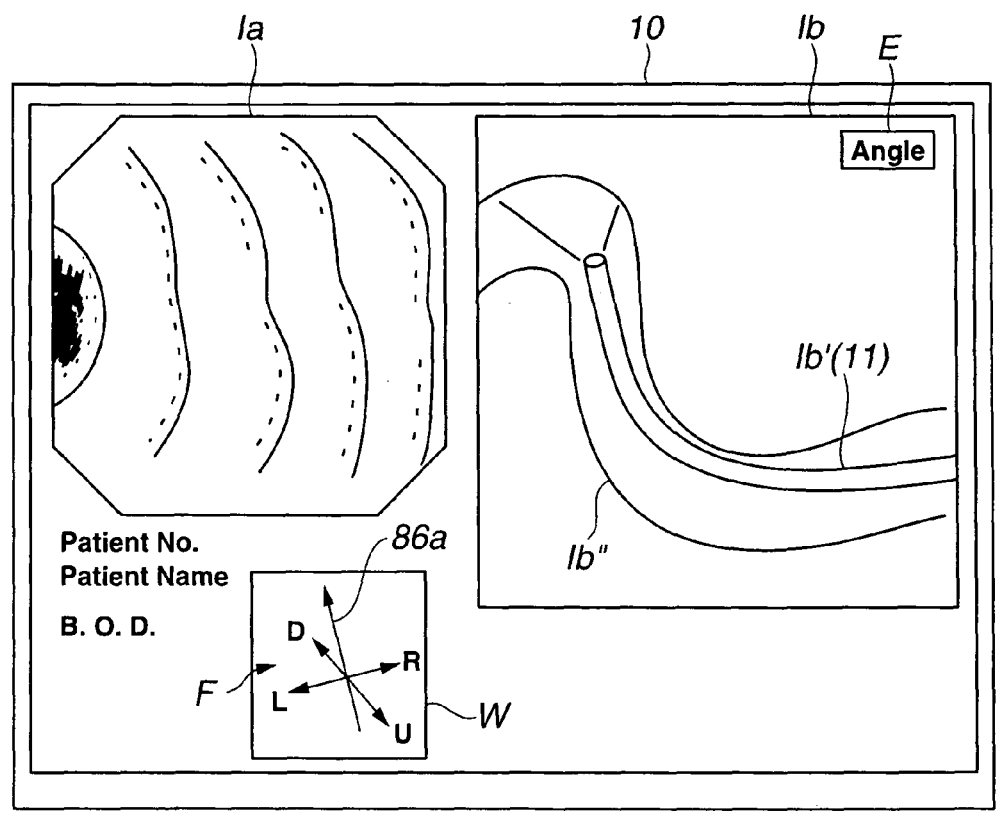
FIG. 15A is a diagram showing a display example of display with an index for bending in a third variation.

In the embodiment 1, the endoscopic image Ia and the UPD image Ib are displayed on the display surface of the high-definition monitor 10 as shown in FIG. 5, but in this variation, as shown in FIG. 15A, an index F for bending is further displayed.

In this variation, in order to facilitate bending operation in the UPD image Ib (more accurately, Ib'), the bending index F associated at least with the axial direction of the distal end side in this UPD image Ib (Ib') is displayed.

In the example in FIG. 15A, the bending index F is displayed in a display frame W below the display area of the endoscopic image Ia.

Figure 15B:
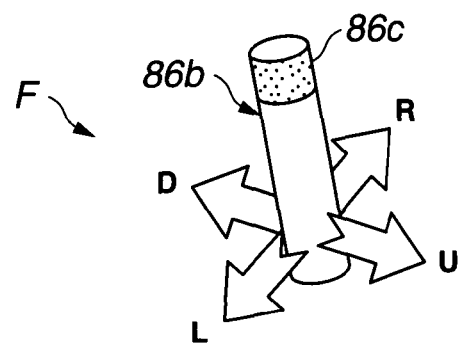
FIG. 15B is a view showing a display example of the index for bending in the variation in FIG. 15A.

As a display example displaying this bending index F, it may be displayed in a simplified form as in FIG. 15A or more specifically as shown in FIG. 15B.

In FIG. 15A, at the base end side of an arrow 86a modeling the direction in display matching the axial direction of the vicinity of the distal end portion of the insertion portion 11 in the UPD image Ib (Ib'), arrows with U, D, R, L are shown indicating bending directions of the up, down, right and left to which the bending portion 16 is actually bent when carrying out bending operation to bend in any of the up, down, right or left direction, for example.

In FIG. 15B, more specifically, a scope model 86b in the columnar shape closer to the shape of the insertion portion 11 is displayed and arrows attached with U, D, R, L are displayed showing the bending directions of up, down, right and left to which the bending portion 16 is actually bent when carrying out the bending operation to the base end side.

Also, FIG. 15B shows a distal end mark 86c displaying the distal end portion of the scope model 86b in a color different from the other portions.

In order to display the above bending index F, the video processing circuit 37 in the video processor 6 in FIG. 1 or the insertion-shape calculation/display processing circuit 47 of the UPD device 8 executes processing for displaying an image of the above bending index F in this variation.

In this variation, in order to display the bending index F, even if the bending operation is to be done by referring to the display on the UPD image Ib side, the bending operation to a desired direction can be done more easily. That is, in this bending index F, the arrow 86a, the scope model 86b or the like is displayed in the direction matching the axial direction of the distal end portion in the actually displayed UPD image Ib, and when the bending operation is to be made in the axial direction, since the bending direction to be actually bent is displayed, the operator can make bending easily in the desired direction by referring to this bending index F.

The bending index may be displayed only when the bending mode corresponding to the UPD image Ib is selected.

Figure 16:
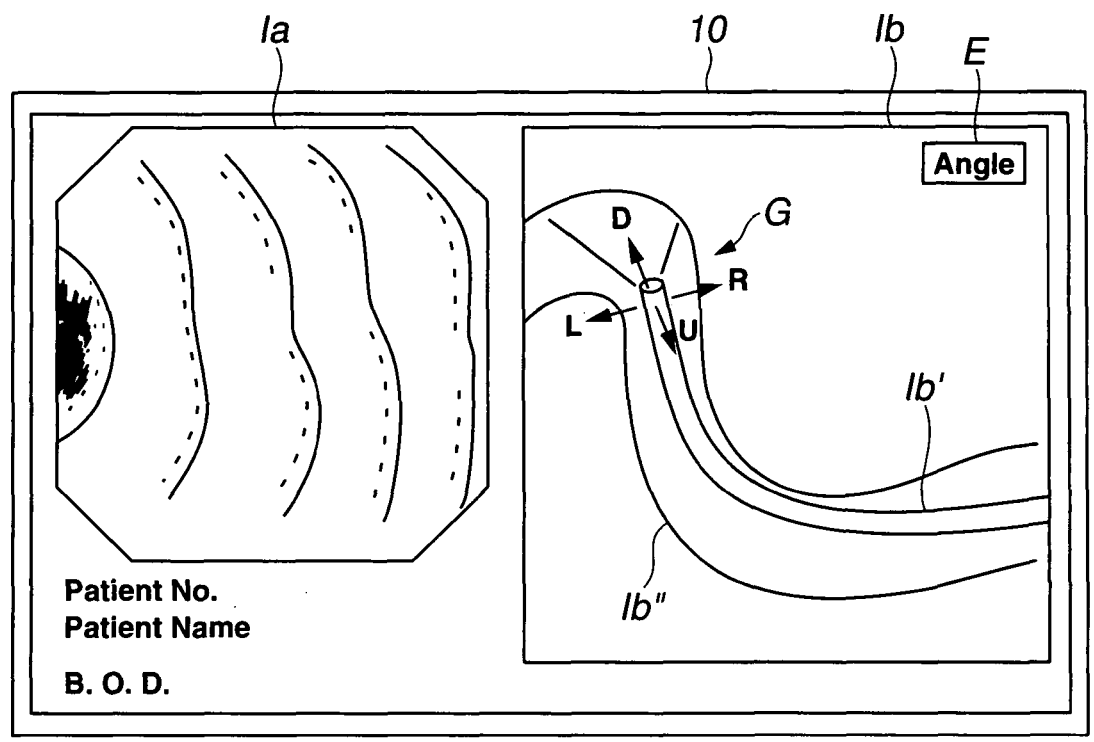
FIG. 16 is a diagram showing a display example of display with an index for bending in a fourth variation.

Instead of displaying the bending index F on the display area side of the endoscopic image Ia as in the third variation shown in FIGS. 15A, 15B, display may be made as in a fourth variation shown in FIG. 16. In the case of FIG. 16, a bending index G indicating the direction to be bent vertically, horizontally at bending operation is displayed in a periphery portion of the distal end portion on the UPD image Ib' (Ib'), for example.

When the bending index G is displayed in this way, the operator can also execute bending operation easily to the desired direction from the display of this UPD image Ib (Ib').

Figure 17:
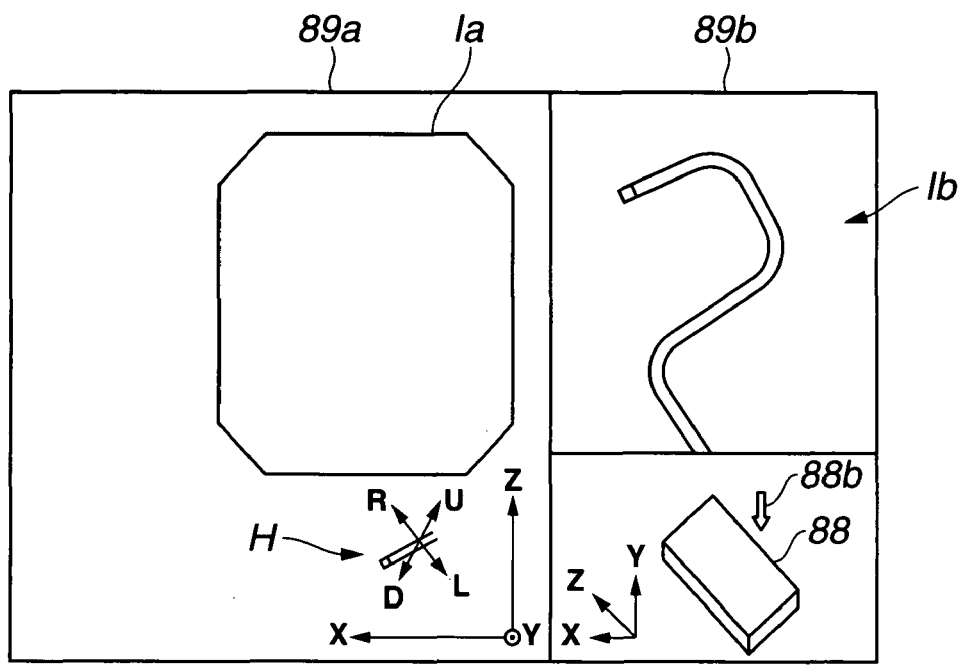
FIG. 17 is a diagram showing a display example of display with an index for bending in a fifth variation.

Alternatively, a display may be as in a fifth variation shown in FIG. 17. In FIG. 17, a bed 88 on which a patient lies down is displayed below the UPD image Ib, for example, and a coordinate system XYZ set in correspondence with the direction of the bed 88 is displayed, and a view direction for displaying the UPD image Ib is indicated by an arrow 88b.

Also, in a display area on the lower part, for example, of the endoscopic image Ia, a bending index H is displayed together with the above coordinate system XYZ.

By displaying in this way, bending can be made easily in a desired direction as in the third variation and moreover, the direction of the neighborhood of the distal end portion of the insertion portion can be grasped with respect to the direction of the body of the patient.

In FIG. 15A and the like, the endoscopic image Ia, the UPD image Ib, the bending index F and the like are displayed on the common screen, but as shown in FIG. 17, for example, display may be made separately by a display screen 89a on the endoscopic image Ia side and a display screen 89b on the UPD image Ib side, or on a separate monitor or the like.

Though the bending-mode selection switch 19 as a selection portion is provided at the endoscope 2 in this embodiment, it may be provided at the video processor 6 and the like other than the endoscope 2. Also, a display screen selection portion may be provided so as to selectively display either of the endoscopic image Ia or the UPD image Ib. And according to the selection of this display screen selection portion, the bending control device 5 may carry out control so as to switch the bending control mode between the first bending mode and the second bending mode.

Second Embodiment

Figure 18:
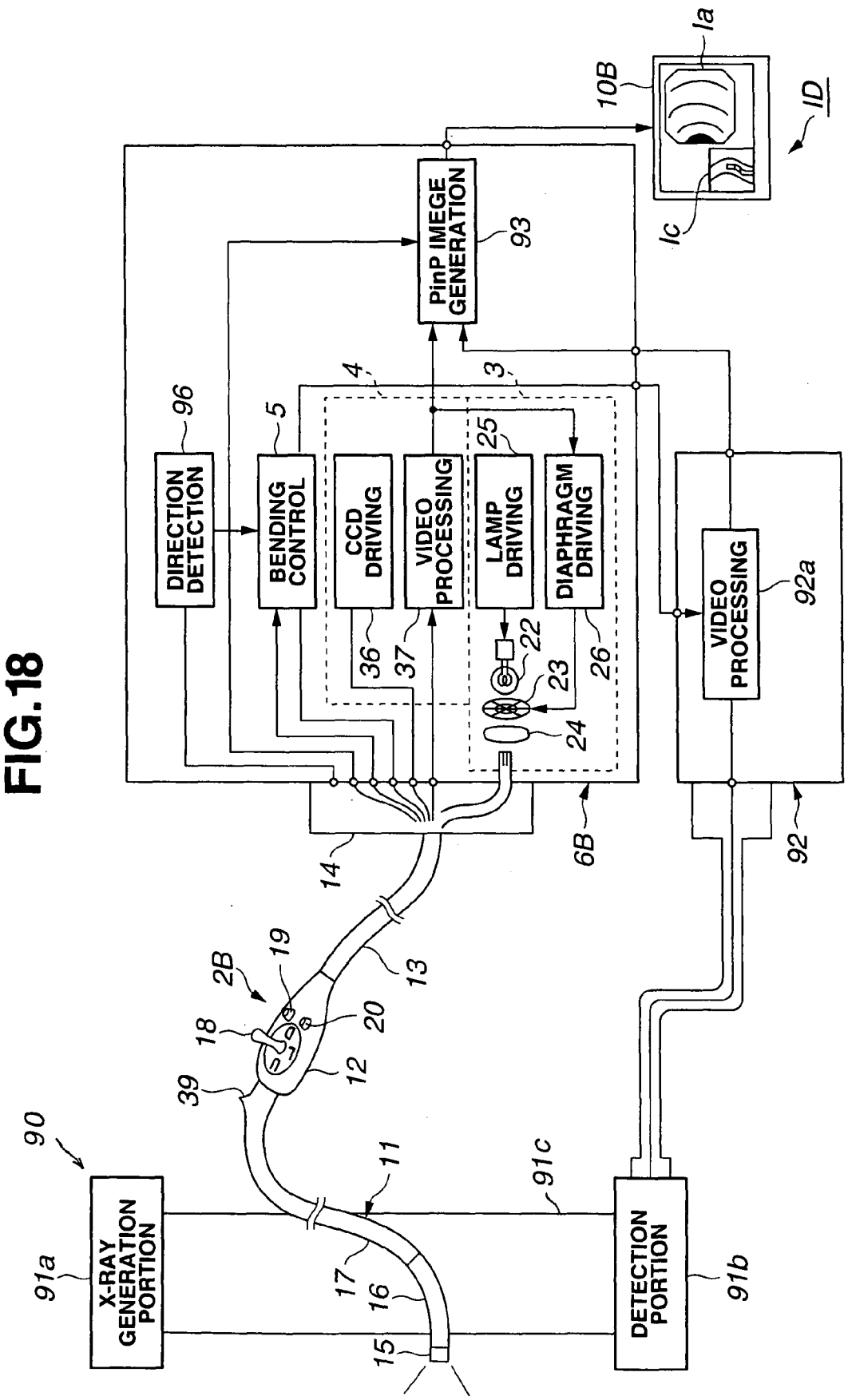
FIG. 18 is a configuration showing an endoscope device provided with a second embodiment of the present invention.

Next, a second embodiment of the present invention will be described referring to FIG. 18. FIG. 18 shows an endoscope device ID provided with the second embodiment. This endoscope device ID employs an X-ray device 90 instead of the UPD coil unit 7 and the UPD device 8.

In this X-ray device 90, an X-ray generation portion 91a and a detection portion 91b for detecting its transmitted X-ray are supported by a support member 91c in the opposed manner, between which a patient can lie down.

A signal having converted by the detection portion 91b to an electric signal is inputted to an X-ray processor 92 and converted to a video signal corresponding to an X-ray image by a video processing circuit 92a inside it. Also, in this endoscope device ID, a parent-child image generation circuit (PinP image generation circuit) 93 is incorporated inside a video processor 6B, for example, and a video signal of a PinP image with an image from the video processing circuit 37 as a parent image and an X-ray image from the X-ray processor 92 as a child image is generated and outputted to the monitor 10B.

On the monitor 10B, the endoscope image Ia and the X-ray image Ic are displayed as the PinP image.

The PinP image generation circuit 93 is capable of selection through operation of the scope switch 20, for example, among display of parent and child images inverted, display of only one of the images or display of both in the same size adjacently.

Also, an endoscope 2B in this embodiment is in the structure not having the UPD coil 41 in the endoscope 2 in the first embodiment. Also, in order to enable bending control in the bending mode corresponding to the X-ray image Ic, a direction sensor 95 (See FIG. 19) for detecting the direction of the distal end portion 15 is provided inside the distal end portion 15.

This direction sensor 95 is connected to a direction detection circuit 96 in the video processor 6B through a signal line for direction detection, information indicating the direction of the distal end portion 15 is generated by the direction detection circuit 96 and this information is inputted to (a control portion of) the bending control device 5.

This control portion executes direction correction processing as in the first embodiment using this information when the bending mode corresponding to the X-ray image Ic is selected. In the X-ray device 90 in this embodiment, it is assumed that the X-ray generation portion 91a and the detection portion 91b are used in the state where they are arranged vertically (perpendicularly) as shown in FIG. 18, and in this case, the image capturing direction of the X-ray image Ic is fixed to the perpendicular direction.

However, if the X-ray image Ic is to be displayed, the display direction is changed by the control from the bending control device 5 so that the bending instructed direction by the bending control means matches the bending instructed direction determined from the screen. More specifically, by the control from the bending control device 5, rotation control of the X-ray image Ic is executed, for example.

And as shown in the X-ray image Ic in FIG. 18, the image rotation processing is executed by an image rotation processing circuit in the image processing circuit 92a for the display direction of the X-ray image Ic so that the axial direction of the distal end side of the insertion portion in the image becomes substantially the up direction. The X-ray image Ic inputted to the video processor 6B may be given rotation processing in this video processor 6B.

Figure 19:
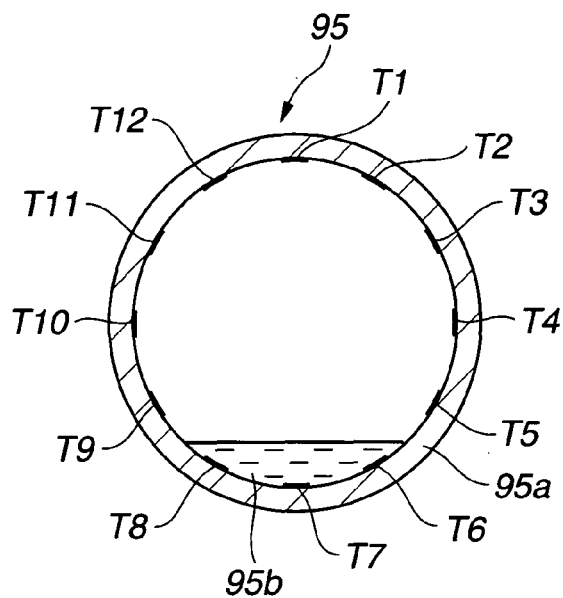
FIG. 19 is a view showing a configuration of a direction sensor.

FIG. 19 shows a structure of the above direction sensor 95. A storing portion 95a with the sectional face in the annular shape as shown in FIG. 19 is formed at the distal end portion 15, and a conductive fluid 95b such as salt water is stored inside it.

On the inner circumferential surface of the storing portion 95a, electrodes T1, T2 . . . , T12 are provided with a predetermined interval, and each electrode Ti is connected to the direction detection circuit 96 through its respective signal line. The direction detection circuit 96 becomes detection information on which the vertical and horizontal positions in the distal end portion 15 is located in the gravity direction (lower position in the perpendicular direction) from information on a contact which is made conductive by the conductive fluid 95b.

In this embodiment, too, the operator can perform bending operation in the bending mode corresponding to the endoscopic image Ia as well as the bending operation in the bending mode corresponding to the X-ray image Ic.

Other than the X-ray image Ic, an MRI image by a magnetic resonance imaging device (MRI device) or an ultrasonic image from outside the body can be similarly used and given bending control in the bending mode corresponding to the respective image. Also, as will be mentioned below, bending control may be made in the bending mode corresponding to an image by a computer tomography (CT) device.

Third Embodiment

Next, a third embodiment of the present invention will be described referring to FIG. 20. In this embodiment, instead of the X-ray device 90 for obtaining an X-ray image Ic in a given direction in the second embodiment, for example, a CT device 101 is used in which a CT body 101a provided with the X-ray generation portion 91a and the detection portion 91b oppositely supported are made rotatable by a motor 106 (in FIG. 20, the CT body 101a is schematically depicted in the semi-cylindrical shape) so that an X-ray image is obtained from a different direction to generate a CT image Id by an X-ray of an arbitrary section.

When the monitor 10B displays the CT image Id, control for automatic setting is made such that the display surface at the distal end side of the insertion portion 11 includes the axial direction at the distal end side of the insertion portion 11 and thus, includes the traveling direction of a lumen into which the distal end side is inserted so as to improve operability in insertion work involving bending operation.

Figure 20:
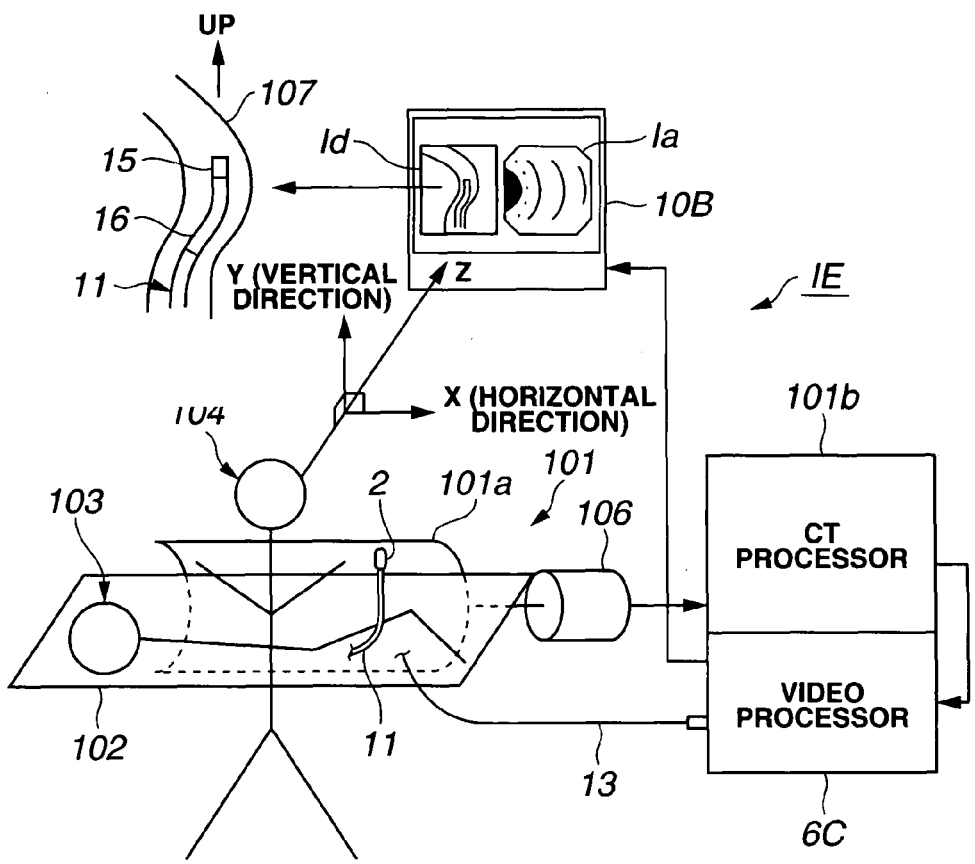
FIG. 20 is a configuration showing an outline of an endoscope device provided with a third embodiment of the present invention.

FIG. 20 schematically shows a configuration of an endoscope system 1E provided with the third embodiment, in which a patient 103 lies down on a bed 102 in the lateral position and an operator 104 opposed to one side of the bed 102 inserts the insertion portion 11 of an endoscope 2C into the body of the patient 103 for endoscopic inspection.

The universal cord 13 of this endoscope 2C is connected to a video processor 6C. Also, the monitor 10B is arranged opposite to the other side of the bed 102 and displays the endoscopic image Ia and the CT image Id by an X-ray adjacently in right and left. Also, a CT processor 101b connected to the CT body 101a for image processing to generate the CT image Id generates the CT image Id of an arbitrary section from an image from a different direction.

This CT image Id is inputted to the video processor 6C, and this video processor 6C generates the endoscopic image Ia from a signal image-captured by the CCD, synthesizes the endoscopic image Ia and the CT image Id and outputs it to the monitor 10B.

An output signal of the X-ray processor 92 is inputted to the video processor 6B in the second embodiment, but an output signal of the CT processor 101b is inputted to this video processor 6C. That is, this video processor 6C is provided with a similar function as that of the video processor 6B. As described in the first embodiment, in bending control by the UPD image Ib, the display direction of the UPD image Ib is associated with the predetermined direction of the joystick 18 as the bending operating means in the relation to be easily operated, and when the insertion portion 11 is twisted or the like, the twist amount is corrected for the bending control.

Similarly, in the CT device 101, too, the output of the direction sensor 95 arranged in the distal end portion 15 of the insertion portion 11 is used to detect in which (circumferential) direction the distal end portion 15 is located, and a sensor (107) for detecting the axial direction of the distal end portion 15 is also provided in the distal end portion 15 in this embodiment.

Figure 21:
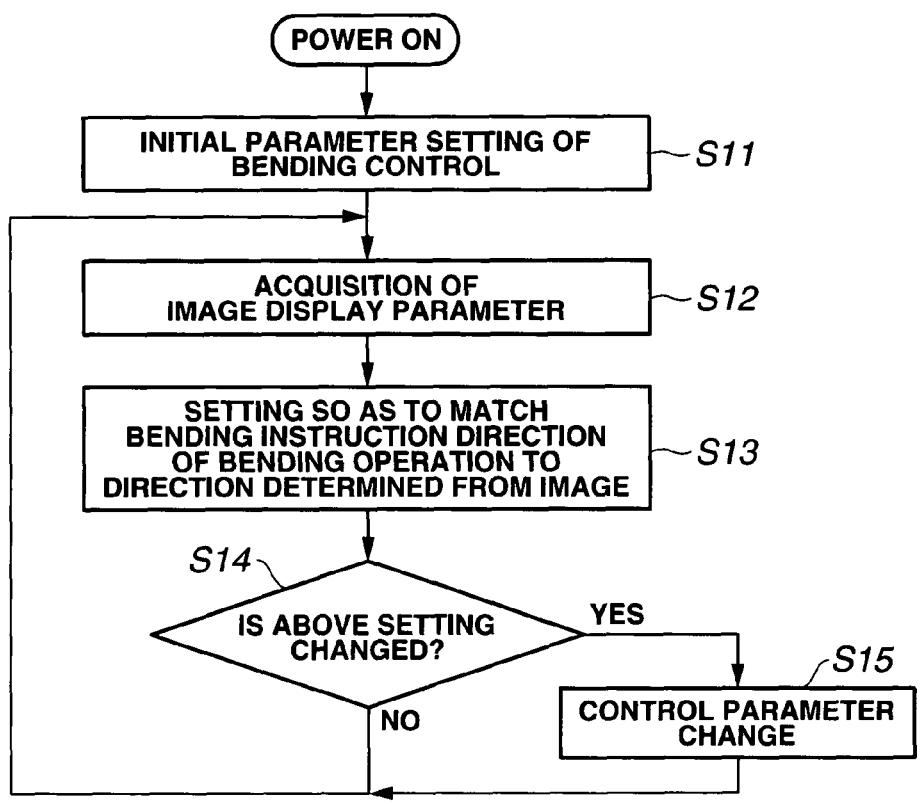
FIG. 21 is a flowchart showing an operation content in a bending mode corresponding to a CT image by a bending control device.

And by processing as shown in FIG. 21, display is made (See the CT image Id in FIG. 20) including the axial direction at the distal end side of the insertion portion 11 and the lumen traveling direction in the display surface and the display direction is matched to the bending instruction direction of the bending operation means for easier bending control. Next, action of this embodiment will be described. The same reference numerals are used in the description for the constituent elements described in the first embodiment or the second embodiment.

When powered on, as shown in Step S11 in FIG. 21, the CPU 68a forming the control portion 68 in the bending control device 5 sets initial parameters for the bending control. Here, an initial value of a parameter corresponding to the bending amount is set supposing that bending has not been made at the first.

Figure 22:
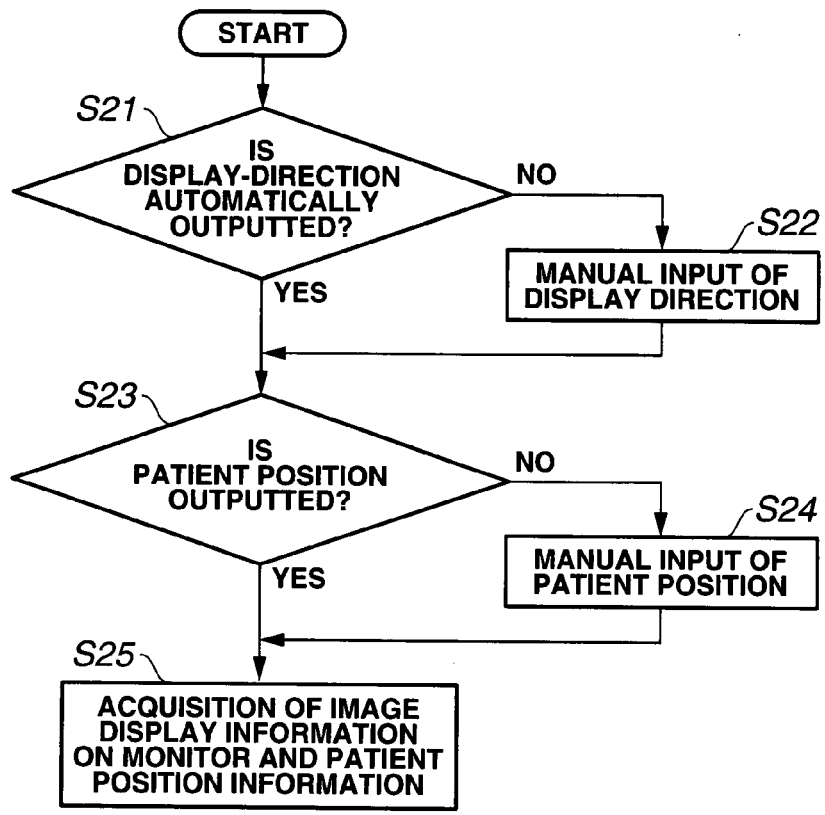
FIG. 22 is a flowchart showing an operation content when an image display parameter is obtained in FIG. 21.

At the subsequent Step S12, the CPU 68a obtains an image display parameter. In order to obtain this image display parameter, processing in FIG. 22 is executed. As will be mentioned later, by the processing in FIG. 22, information can be obtained regarding from which direction the displayed image sees the patient 102 in an image, which circumferential position of the distal end portion 15 of the insertion portion 11 is the vertical direction and how the axial direction of the distal end portion 15 is physically inclined with respect to the vertical position.

At the subsequent Step S13, the CPU 68a refers to the information in Step S12 and makes setting to match (associate) the bending instruction direction by the bending operating means such as the joystick 18, a track ball or the like to the bending instruction direction determined from the actual display image.

Specifically, by this setting, as in the description in the first embodiment, the operator looks at the CT image Id on the monitor 10B and gives operation to instruct the bending direction by tilting the joystick 18 in the desired direction to bend the distal end side of the insertion portion 11 form the CT image Id. Then, the CPU 68a of the control portion 68 is bending-controlled so that the bending portion 16 is actually bent in the instructed direction determined by the CT image Id. Then, the CPU 68a of the control portion 68 carries out bending control so that the bending portion 16 is actually bent to the instructed direction determined by the CT image Id.

Also, in this Step S113, setting processing is executed to match the display of lumen traveling direction to the bending instruction direction by the CPU 68a.

In the case of the CT device 101, even if the supplementary image generation circuit 48 in the case of the UPD image Ib is not provided, the lumen shape is displayed on the transmitted image by the X ray in the accompanied manner as a supplementary image. In this case, the lumen traveling direction is also displayed substantially along the direction to which the distal end side of the insertion portion 11 is inserted only by setting as in step S13 (of course, if the lumen portion as the deep side to which the insertion portion 15 is to be inserted is bent at a position close to the distal end portion 15, the lumen traveling direction is in the direction out of the direction of the distal end side of the insertion portion 11 in that portion). When the profile of the lumen shape is hard to be grasped, the supplementary image may be displayed as in the case of the UPD image Ib.

At the subsequent Step S14, the CPU 68a determines if the setting in Step S13 is (needed to be) changed or not. If the up, down, right or left direction of the bending direction instructing means is not to be changed, the routine goes back to Step S12.

If the up, down, right or left direction of the bending direction instructing means is not to be changed, the up, down, right and left direction is not changed all the time with respect to the operation portion or the like where the bending direction instructing means is provided, and a wrong bending instruction direction is not inputted when the way to hold the operating means such as the operation portion is set uniquely according to the right-handed or left-handed.

On the other hand, if the up, down, right or left direction of the bending direction instructing means is to be changed, as shown in Step S116, a control parameter is changed according to the change.

When the up, down, right or left direction of the bending direction instructing means is to be changed, bending operating means such as a track ball which is provided on the operation panel or can be arranged at an arbitrary position (which will be described later) is suitable.

In this bending control, even if the patient position is changed, by operating the bending operating means such as the joystick 18 in the desired direction to bend determined from the CT image Id all the time, bending control can be made to actually drive/bend the bending portion 16 in the desired direction to bend determined from the CT image Id.

Next, processing of the Step S12 will be described referring to FIG. 22. When the processing to obtain the image display parameter is started, the CPU determines, as shown in Step S21, if information on the display direction of the CT image Id to be a reference should be automatically outputted by (the CT processor 101b of) the CT device 101.

As an output format when the CT device 101 automatically outputs the information in the image display direction, information may be outputted for A-P (direction from front to back of the patient 103), L-R (when the body of the patient 103 is seen from the left side of the patient 103), R-R (when the body of the patient 103 is seen from right side of the patient 103), P-A (when the body of the patient 103 is seen from the back of the patient 103) or information obtained when rotation is made clockwise by 30 degrees from each reference, for example.

On the other hand, when the information on display direction is not automatically outputted by the CT device 101, the operator manually inputs the display direction as shown in Step S22.

The input format in the case of this manual input may be made by inputting information such as A-P, L-R, R-R, P-A or information after clockwise by 30 degrees from each reference, for example, to the bending control means.

Since it is preferably interlocked with change in the patient position, at Step S23 after Step S21 or S22, the CPU determines if there is an output of information on the patient position direction from the CT device 101.

If the information on the patient position direction is outputted, the routine goes on to Step S25, while if there is no information on the patient position direction is outputted, the routine goes on to Step S25 after processing of manual input of the information on the patient position in Step S24.

At Step S25, the CPU obtains the information on image display direction on the monitor 10B and the patient position information after processing from Step S21 to step S24.

In the case of Step S23, since the display direction can be outputted real time with respect to a change in the patient position at insertion of the insertion portion 11 in the normal CT device 101, the CPU 68a constituting the control portion 68 can easily interlock the bending control in the vicinity of the distal end portion 15 by using the information.

When the operator such as the operator 104 gives an instruction on the bending direction, as shown in FIG. 20, the operator is observing the monitor 10B on which the endoscopic image Ia or the CT image Id is displayed. Thus, the direction of an axis substantially parallel with an axis connecting the position of the operator and the direction of the monitor 10B (for observation) may be allocated to the vertical direction (up and down direction) on the displayed screen and the substantially horizontal direction perpendicular to the above axis (direction separated from the axis) to the horizontal direction on the screen.

In this case, when the operator performs bending operation while paying attention to the traveling of an intestine in the CT image Id on the monitor 10B and the shape of the distal end side of the insertion portion 11 (bending mode of the CT image Id), however much the insertion portion 11 is twisted (since as shown in a partially enlarged view of the CT image Id in FIG. 20, the lumen 107 is bent to the left side in the vicinity of the distal end portion 15 with respect to the distal end portion 15 of the insertion portion oriented upward), the bending operation to the left direction can be made most easily without sense of discomfort as the feeling to look at this CT image Id.

The case where the bending operating means such as the joystick 18 is provided at the operation portion 12 of the endoscope 2 has been mainly described above, but there may be a case where the bending operating means is provided at the video processor 6C or the operation panel of the bending control device 5 or there may be also a case of a remote control type bending operating means.

Therefore, an output control value for the above bending direction control may be corrected by detecting a rotation amount of the insertion portion 11 of the endoscope.

Figure 23A:
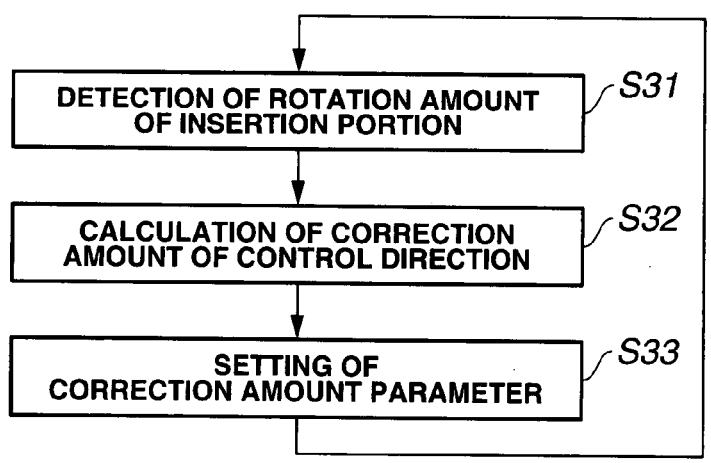
FIG. 23A is a flowchart showing an operation content of bending control by detecting a rotation amount of twist or the like of the insertion portion.

FIG. 23A shows an outline of control processing of this case. At Step S31, the CPU detects a rotation amount of the insertion portion 11 of the endoscope 2 (detects by output of the direction sensor 95, for example). And based on the detection information, the CPU 68a calculates a correction amount in the bending direction as shown in Step S32, and at the subsequent Step S33, change setting of the correction amount parameter to be corrected by the calculated correction amount is made and the routine goes back to Step S31. In this way, even if the insertion portion 11 of the endoscope 2 is rotated (twisted), favorable bending operation and bending control can be performed without being affected by that.

When the operator such as the operator 104 sets allocation of the bending instruction direction to give an instruction of the bending direction, it is preferable that setting is made to be easily used by the operator.

In this case, the following allocation may be made other than the above allocations associated with the monitor screen.

Figure 23B:
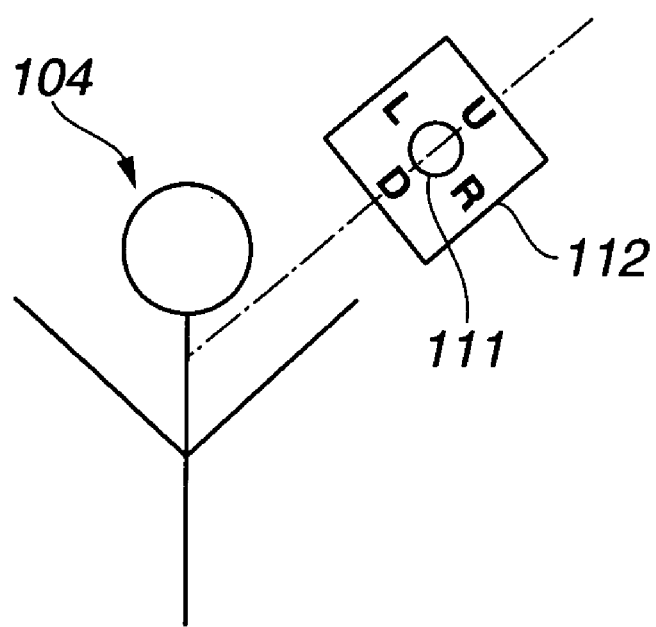
FIG. 23B is an explanatory view of a positional relation between and operator and a remote control to which bending instruction operation is applied by the operator.

As shown in FIG. 23B, with the position of the operator such as the operator 104 at the center, a line connecting the bending instruction operation means by a remote control 112 provided with a track ball 111 and the position of the operator is set as the center axis, and allocation of the instruction in the vertical direction to the substantially center axis and the operation in the horizontal direction to the axial direction substantially perpendicular to the center axis will best match the human operation feeling.

When the bending instruction operation means is arranged at a position where an arm is stretched the most, the substantial arc within which the stretched arm can be moved corresponds to the horizontal direction, but since the operation with the stretched arm forces an extremely improper posture in terms of ergonomics, it is preferable that the bending instruction operation means exists in a range where a slightly bent arm can reach.

Such a line connecting the operator's position to the operation input means is set as the basic axis, and the direction separated from the axis may allocated to the horizontal direction of the bending instruction and the direction separating, approaching on the substantial center axis to the vertical direction of the bending instruction.

It is difficult to detect the position of the operator all the time, but since a distance between the bending instruction operation means and the operator is separated only to the extent of the distance of an arm in terms of the operation, the position of the substantial bending instruction operation input means and the position of the monitor 10B can be used for the positions of the operator and the monitor 10B.

The position of the monitor 10B and the position where the bending instruction operation means is arranged are extremely rarely arranged at the same height in actuality.

Thus, when the vertical direction and the horizontal direction are to be matched strictly, the axis connecting the bending instruction operation means to the monitor is projected on the ground as the horizontal surface, and the projected axis is set as the axis for bending in the vertical direction on the screen. Also, the direction perpendicular to the projected axis can be set as the operation axis in the horizontal direction.

However, if the axis connecting the bending instruction operation means and the monitor 10B is not much inclined with the ground as the horizontal face, such a method may be employed that the axis itself connecting the bending instruction operation means and the monitor 10B is used for the bending in the vertical direction on the display screen instead of the axis projected on the horizontal surface and the axis in the horizontal surface perpendicular to the axis connecting the bending instruction operating means to the monitor 10B is allocated to the bending in the horizontal direction.

Alternatively, the allocation of these two control directions may be set by arbitrary switching by the operator.

According to this embodiment, as with the first embodiment and the like, the work to insert the insertion portion 11 of the endoscope 2 into a bent body cavity can be performed smoothly. Also, depending on the preference of the operator, the bending instruction operation can be performed in the convenient state, which can realize a usable system.

In this embodiment, the case of the CT device 101 has been described, but the present invention may be applied to a case using the UPD device 8 and other devices.

Also, provision of the bending control means for bending control corresponding to a second image such as the UPD image Ib described in this embodiment on the existing bending control device for normal bending control, and employment of the bending control method also belong to the present invention. Moreover, a plurality of bending control means may be provided so that one of them is operated in actual use.

In this way, according to the present invention, such an effect is exerted that operability of the bending operation at insertion or the like of the insertion portion 11 can be improved.

Embodiments constituted by partially combining the above-mentioned embodiments also belong to the present invention.

What is claimed is:

1. A bending control device comprising:
a bending instruction operation portion for executing bending instruction operation to a bending portion in an endoscope having an insertion portion provided with an image pickup portion for capturing an image and the bending portion capable of being bent at the distal end side; and
a bending control portion for controlling bending of the bending portion according to the bending instruction operation by the bending instruction operation portion, wherein
the bending control portion includes, as bending control modes for the bending control of the bending portion:
a first bending control mode for bending control corresponding to a first image captured by the image pickup portion; and
a second bending control mode for bending control corresponding to a second image displaying the distal end side of the insertion portion, and
the bending control device further comprises a display portion of an index for bending indicating a bending direction corresponding to indication of the distal end side of the insertion portion in the second image when at least the second bending control mode is selected.

2. The bending control device according to claim 1, further comprising a selection device for selecting one of the first and the second bending control modes.

3. The bending control device according to claim 2, further comprising an information display device for displaying information selected by the selection device.

4. The bending control device according to claim 1, further comprising a direction display portion for displaying a direction to which the bending portion is bent in at least one of the first image and the second image, when the bending instruction operation is executed by the bending instruction operation portion.

5. The bending control device according to claim 1, wherein the image pickup portion is fixed at the distal end portion of the insertion portion in a predetermined relation with the bending direction of the bending portion, and the first image captured by the image pickup portion and displayed on the image display device is displayed with the up direction of the first image in the up direction all the time, and the up direction of the first image corresponds to the up bending direction of the bending portion.

6. The bending control device according to claim 5, wherein the bending control portion executes bending control so that the bending portion is bent in the direction of the bending instruction operation by the bending instruction operation portion for the bending portion in which the up direction of the first image is associated with the up bending direction of the bending portion and the other directions are also associated respectively.

7. The bending control device according to claim 1, wherein the second image displayed on the image display device is displayed so that the axial direction of the distal end portion of the insertion portion in the second image becomes a predetermined direction in the image display device.

8. The bending control device according to claim 7, wherein the predetermined direction is displayed on the image display device so that the axial direction of the distal end portion is the vertical direction and the distal end side of the insertion portion is oriented upward.

9. The bending control device according to claim 1, further comprising a direction detecting device for detecting the axial direction of the distal end portion and the circumferential direction around the axial direction.

10. The bending control device according to claim 7, further comprising a direction detecting device for detecting the axial direction of the distal end portion and the circumferential direction around the axial direction, wherein the bending control portion executes bending control so that the bending portion is bent in the direction of the bending instruction operation by the bending instruction operation portion by referring to a detection result of the axial direction and the circumferential direction of the distal end portion detected by the direction detecting device.

11. The bending control device according to claim 1, further comprising a supplementary image display portion for displaying a supplementary image in a body cavity into which the insertion portion is inserted in correspondence to the second image.

12. The bending control device according to claim 1, further comprising a calculation portion for calculating a discrepancy amount between a predetermined direction in a displayed image of the distal end side of the insertion portion in the second image and a predetermined direction at the distal end side of the actual insertion portion in correspondence with selection of the second bending control mode, wherein the bending control portion executes bending-driving by correction on the basis of the discrepancy amount when the bending portion is to be bent.

13. The bending control device according to claim 12, wherein the predetermined direction in the displayed image of the distal end side of the insertion portion in the second image is not changed with respect to rotation of the distal end side of the actual insertion portion around its center axis, and the display direction of the first image is changed according to the rotation amount of the distal end side of the actual insertion portion around its center axis.

14. The bending control device according to claim 1, wherein the second image is an image displaying a shape of at least the shape of the distal end side in the insertion portion using the detection result by a position detecting device incorporated in the insertion portion.

15. The bending control device according to claim 1, wherein the second image is an X-ray image displaying an image including the distal end side of the insertion portion by transmission of an X-ray.

16. The bending control device according to claim 1, wherein the second image substantially includes the axial direction of the distal end side of the insertion portion in the display surface and a traveling direction of a lumen portion into which the vicinity of the distal end portion is inserted is also substantially included in the display surface.

17. The bending control device according to claim 1, further comprising an image display device for displaying the first image and the second image at the same time.

18. The bending control device according to claim 1 wherein the display portion of the bending index displays the axial direction of the distal end side of the insertion portion and a direction to which the axial direction is bent.

19. A bending control device comprising:
a bending instruction operation portion for executing bending instruction operation to a bending portion in an endoscope having an insertion portion provided with an image pickup portion for capturing an image and the bending portion capable of being bent at the distal end side; and
a bending control portion for controlling bending of the bending portion according to the bending instruction operation by the bending instruction operation portion, wherein
the bending control portion includes, as bending control modes for the bending control of the bending portion:
a first bending control mode for bending control corresponding to a first image captured by the image pickup portion; and
a second bending control mode for bending control corresponding to a second image displaying the distal end side of the insertion portion, and
the bending control device further comprises a calculation portion for calculating a discrepancy amount between a predetermined direction in a displayed image of the distal end side of the insertion portion in the second image and a predetermined direction at the distal end side of the actual insertion portion in correspondence with selection of the second bending control mode, wherein the bending control portion executes bending-driving by correction on the basis of the discrepancy amount when the bending portion is to be bent.

20. A bending control device comprising:
a bending control portion for executing control of a bending direction of a bending portion of an endoscope provided with an image pickup device and the bending portion; and
a bending instruction operation portion for executing an bending instruction operation in the direction to bend the bending portion,
wherein the bending control portion executes controlling bending of the bending portion by switching between:
a first bending control mode defined to bend the bending portion so that the bending instruction operation portion bends the bending portion in a vertical direction corresponding to a predetermined direction that serves as a reference when displaying on a display device a first observation image obtained by the image pickup device; and
a second bending control mode defined to bend the bending portion so that the bending instruction operation portion bends the bending portion in a vertical direction corresponding to a predetermined direction that serves as a reference on a second observation image when a state of the distal end of the insertion portion is displayed on the display device.

21. The bending control device according to claim 20, further comprising
a selection portion operated by an operator for selecting either of the first bending control mode and the second bending control mode,
wherein the bending control portion executes controlling bending of the bending portion in either of the first bending control mode and the second bending control mode according to selection of the selection portion.

* * * * *